United States Patent
Nagele

(10) Patent No.: US 11,187,708 B2
(45) Date of Patent: Nov. 30, 2021

(54) EARLY STAGE PARKINSON'S DISEASE DIAGNOSTIC KITS AND METHODS

(71) Applicant: ROWAN UNIVERSITY, Glassboro, NJ (US)

(72) Inventor: Robert G. Nagele, Turnersville, NJ (US)

(73) Assignee: Rowan University, Glassboro, NJ (US)

(*) Notice: Subject to any disclaimer, the term of this patent is extended or adjusted under 35 U.S.C. 154(b) by 0 days.

(21) Appl. No.: 16/596,258

(22) Filed: Oct. 8, 2019

(65) Prior Publication Data

US 2020/0041528 A1    Feb. 6, 2020

Related U.S. Application Data

(62) Division of application No. 15/041,573, filed on Feb. 11, 2016, now Pat. No. 10,436,801.

(60) Provisional application No. 62/114,971, filed on Feb. 11, 2015.

(51) Int. Cl.
*G01N 33/68* (2006.01)
*G01N 33/564* (2006.01)

(52) U.S. Cl.
CPC ....... *G01N 33/6896* (2013.01); *G01N 33/564* (2013.01); *G01N 2800/2835* (2013.01)

(58) Field of Classification Search
CPC ............. G01N 33/6896; G01N 33/564; G01N 2800/2835
See application file for complete search history.

(56) References Cited

U.S. PATENT DOCUMENTS

| 9,664,687 B2 | 5/2017 | Nagele |
| 2003/0068659 A1 | 4/2003 | Kilgannon et al. |
| 2014/0017303 A1 | 1/2014 | Navon et al. |
| 2014/0045915 A1 | 2/2014 | Skog et al. |
| 2014/0364328 A1 | 12/2014 | Nagele |

FOREIGN PATENT DOCUMENTS

| WO | 2011072247 A2 | 6/2011 |
| WO | 2012045324 A1 | 4/2012 |
| WO | 2013122609 A1 | 8/2013 |
| WO | 2014001576 A2 | 1/2014 |
| WO | 2014009747 A1 | 1/2014 |

OTHER PUBLICATIONS

Han et al., PLoS ONE, 7(2):e32383, Feb. 2012.*
Invitrogen ProtoArray® Human Protein Microarrays brochure, "Absolute identification of novel autoimmune biomarkers" (2009) and attached list of antigens from Invitrogen technical support.*
ProtoArray v5 content list (2010). Published online at <www.invitrogen.com> Retrieved on Nov. 25, 2016.
Devos et al., Clinical Therap, 35(10):1640-1652, 2013.
Riedererand Laux, Experimental Neurobiology, 2: 1-17, Mar. 2011.
Nagele et l., "Brain reactive autoantibodies prevalent in human sera increase intraneuronal amyloid beta 1-42 deposition," J Alzheimers Dis (Apr. 2011): 25(4):605-622.
Yanamandra et al., "a-synuclein reactive antibodies as diagnositc biomarkers in blood sera of Parkinson's desiease patients," PLoS One (Apr. 25, 2011); 6(4):e18513.
Hong et al. Brain: a journal of neurology 133, 713-726 (2010).
Gerlach et al. Journal of neural transmission 119, 39-52 (2012).
van Dijk et al. European journal of neurology : the official journal of the European Federation of Neurological Societies 21, 388-394 (2014).
Mollenhauer et al. Experimental neurology 213, 315-325 (2008).
Aerts et al. Neurobiology of aging 33, 430 e431-433 (2012).

* cited by examiner

*Primary Examiner* — Kimberly Ballard
*Assistant Examiner* — Stacey N MacFarlane
(74) *Attorney, Agent, or Firm* — Fox Rothschild LLP

(57) ABSTRACT

The present invention relates to diagnostic methods, reagents, and kits for detecting and diagnosing Early Stage Parkinson's disease.

9 Claims, 5 Drawing Sheets

Specification includes a Sequence Listing.

SEQUENCE LISTING

<160> NUMBER OF SEQ ID NOS: 7

<210> SEQ ID NO 1
<211> LENGTH: 5336
<212> TYPE: DNA
<213> ORGANISM: Homo sapiens

<400> SEQUENCE: 1

```
gctgctccgc gcgcagccgg ctcgggccgc tcctcctgac tgaggcgcgg cggcggcggt    60
ggctgtgacc gcgcggaccg agccgagaca ttcgcgccgg gggatcgggc gccgccgccg   120
ctgggccccg ggcgcgtgga tgcggctggg tcgggcggcg ccgtacacct gaggcggaga   180
acggggcgcg gcgcgggtga cgctgtcagg gccgcggttc ctgacgccca ggcgctcgcc   240
aggacgagcc aggcagtgat tgaggcaccg gcttcacctt cacccatggt ccggagagc    300 ctagcgggc tcgccaccgc ctcccggctc cccttccacg cctcatcctg ccagcctcgc   360
cgccccgcca gcgccgggca accgcctcgc ccgaagccct ccctcgttac tgtccgcata   420
ccccggcggc gccgccgcgg gaagcggctc ccctcctct tcctccgcgt cctcttccct   480
cttccccccg ccggggccgc ttgttgcacc gcccgcggc ctgcgggagc cgctcgcccc   540
ggccttgtgc tcgcgtccgc accccttcc tgtcgccccc cggggccgc accacagccc   600 ggccggcgag accccggcca gaccccgctg cccgcacaaa atgtcggccc ggacgccatt   660
gccgacggtg aacgagcggg acacggaaaa tcatacatct gtggatggat atactgaacc   720
acacatccag cctaccaagt cgagtagcag acagaacatc ccccggtgta gaaactccat   780
tacgtcagca acagatgaac agcctcacat tggaaattac cgtttacaaa aaacaatagg   840
gaagggaaat tttgccaaag tcaaattggc aagcacgtt ctaactggta gagaggttgc    900
tgtgaaaata atagacaaaa ctcagctaaa tcctaccagt ctacaaaagt tatttcgaga   960
agtacgaata atgaagatac tgaatcatcc taatatagta aaattgtttg aagttattga  1020
aacagagaag actctctatt tagtcatgga atacgcgagt gggggtgaag tatttgatta  1080
cttagttgcc catggaagaa tgaaagaaa agaggcccgt gcaaaattta ggcagattgt   1140
atctgctgta cagtattgtc atcaaaagta cattgttcac cgtgatctta aggctgaaaa  1200
ccttctcctt gatggtgata tgaatattaa aattgctgac tttggttta gtaatgaatt   1260 tacagttggg aacaaattgg acacattttg tggaagccca ccctatgctg ctcccgagct  1320
tttccaagga agaagtatg atgggcctga agtggatgtg tggagtctgg gcgtcattct   1380
ctatacatta gtcagtggct ccttgccttt cgatggccag aatttaaagg aactgcgaga  1440
gcgagtttta cgagggaagt accgtattcc cttctatatg tccacagact gtgaaaatct  1500
tctgaagaaa ttattagtcc tgaatccaat aaagagaggc agcttggaac aaataatgaa   1560
agatcgatgg atgaatgttg gtcatgaaga ggaagaacta agccatata ctgagcctga    1620 tccggatttc aatgacacaa aaagaataga cattatggtc accatgggct tgcacgaga    1680 tgaaataaat gatgccttaa taatcagaa gtatgatgaa gttatggcta cttatattct    1740
tctaggtaga aaaccacctg aatttgaagg tggtgaatcg ttatccagtg gaaacttgtg  1800
tcagaggtcc cggcccagta gtgacttaaa caacagcact cttcagtccc ctgctcacct  1860
gaaggtccag agaagtatct cagcaaatca gaagcagcgg cgtttcagtg atcatgctgg  1920
tccatccatt cctcctgctg tatcatatac caaaagacct caggctaaca gtgtggaaag  1980
tgaacagaaa gaggagtggg acaaagatgt ggctcgaaaa cttggcagca aacagttgg   2040 atcaaaaagc gagatgactg caagccctct tgtagggcca gagaggaaaa atcttcaac    2100 tattccaagt aacaatgtgt attctggagg tagcatggca agaaggaata catatgtctg   2160
tgaaaggacc acagatcgat acgtagcatt gcagaatgga aaagacagca gccttacgga   2220
gatgtctgtg agtagcatat cttctgcagg ctcttctgtg gcctctgctg tcccctcagc   2280
acgaccccgc caccagaagt ccatgtccac ttctggtcat cctattaaag tcacactgcc   2340
aaccattaaa gacggctctg aagcttaccg gcctggtaca acccagagag tgcctgctgc   2400
```

```
ttccccatct gctcacagta ttagtactgc gactccagac cggacccgtt ttccccgagg    2460
gagctcaagc cgaagcactt tccatggtga acagctccgg gagcgacgca gcgttgctta    2520
taatgggcca cctgcttcac catcccatga acgggtgca tttgcacatg ccagaagggg     2580
aacgtcaact ggtataataa gcaaaatcac atccaaattt gttcgcaggg atccaagtga    2640
aggcgaagcc agtggcagaa ccgacacctc aagaagtaca tcaggggaac caaaagaaag    2700
agacaaggaa gagggtaaag attctaagcc gcgttctttg cggttcacat ggagtatgaa    2760
gaccactagt tcaatggacc ctaatgacat gatgagagaa atccgaaaag tgttagatgc    2820
aaataactgt gattatgagc aaaaagagag atttttgctt ttctgtgtcc atggagacgc    2880
tagacaggat agcctcgtgc agtgggagat ggaagtctgc aagttgccac gactgtcact    2940
taatggggtt cgcttcaagc gaatatctgg gacatctatt gcctttaaga acattgcatc    3000
aaaaatagca aatgagctta agctgtaaag aagtccaaat ttacaggttc agggaagata    3060
catacatata tgaggtacag tttttgaatg tactggtaat gcctaatgtg gtctgcctgt    3120
gaatctcccc atgtagaatt tgcccttaat gcaataaggt tatacatagt tatgaactgt    3180
aaaattaaag tcagtatgaa ctataataaa tatctgtagc ttaaaaagta ggttcacatg    3240
tacaggtaag tatattgtgt atttctgttc attttctgtt catagagttg tataataaaa    3300
catgattgct taaaaacttg tatagttgtc tagatttctg cacctgaatg tatgtttgat    3360
gctttgattt gaaatgttc ttccctgtta tttacattct ggtgggtttt taaaattctt     3420
acctccatca tgcaatttg aaaattgtgt ccagaattaa aagtgcatag aaatagcctt      3480
tacaattgta gcatggacct ttaaaaattg ttttaaaatc ttatttaaat ttaaaccaga    3540
agctgaaaaa tagatcagct ttattataca caaaattatt actgcttatc tttgctcttt    3600
tccttgttat cccgcaaggt ttagttgaga agatacaaaa tgtttacagt gttggcactt    3660
agagttttta aattcaagta catgaaattc agtaatagca ttgccttgag ctaactagga    3720
agtaccggga aaaagttaa atctacatca agtttctttt gaactttgaa gtgttttctg     3780
acccactgct aactgtagca acaaaattta aagaaaaaa acatacttt atctggctat      3840 tataacataa actgtcacgt aggtttgctg ccttcagaat accgcaattt aattgcggga    3900
atataataat attgggactg tttcacagca caaactcatc tttacagtgt tgatcaatgc    3960
atcagttaag aaataatgcc acctcaggaa ttaactggca ttgggaacat ttgcctcatt    4020
ctcctgctat cctcttcatt caccctgcc actgtaatat ctataagtac ttaagagact     4080
tgtgagcaaa acatactatt tataacagta tatgattgat ttatgcttat gtggttgttc    4140
agtttgttcc catgtaactc gtttgtttta aatattttgc cagatttctt gtatttattc    4200
cacatcatta tgcctataat gtgccgcttt gtgattgggc atttgcctac ttttctttca    4260
taattagtga tatatgcgat gtaaaaccac tagtaaaggt acattttaat acttgttatt    4320
ttatactgaa ttagccttgg aggttgactg tgcaatgtta tttactgttg taattactgt    4380
aataccaaca tatgggcccc atctgcacac tcctgaaaaa cagaaagtgt attcaaattt    4440
tatcagttta agaaaataa agctgtgata aatactgtaa ttccaaccta cattagaagg     4500
tctaagtgta ggtgatgtgc cattccataa tggcttccag actagggtga attttatgtt    4560
ctgtactgta ctgtgatgta gctttcttct gtaacagtta tgttttaaaa ttaagtgagt    4620 ttttttttg cctagcaaa gggtggtgtt tgaaaaaaaa aatgtgtagc cccttttaa       4680 cctagtgttc attcaaaaaa aaattgatgc aaatctttat tcactttcac tggtgcacac    4740
```

-continued

```
tgaaatttta cttgaacagt tctcataata aagcacttgt cttttgctct ttatcagaat    4800
gtgaattacc tgttttctgg tacaaaagta ttctgtatga ggagtttatt gtatgtgttc    4860
taaatttagt tggcaaaggg tgaagctgtg aaggttttca agattattga aactatgaag    4920
gtttcttgtc attatgacaa gaaagtttaa tcttttttata ggaattcctg tcactgaaat    4980
acgtttttaa aaaaatagac tcatgtgttt tccacggtag aaactgatat tttttttacat    5040 tttctcactg tggccaactc ttctgtgttt gtagaaagga atttgacttc aatatctttt    5100
atgaactaaa aatgaaatct tgatactcac tttagatttt tcattttatg tgttcatgac    5160
aacataaata tttttcaaag atttagagga attttgcaat gtgtttgcat aaataaatac    5220
cagtttatgt tcaccggcta tgtgatacca ggatttcctt ggcttctgtt gaaatattat    5280
ttgatatgac atcccttata ttaaattaat tattttgtaa aaaaaaaaaa aaaaaa       5336
```

<210> SEQ ID NO 2
<211> LENGTH: 795
<212> TYPE: PRT
<213> ORGANISM: Homo sapiens

<400> SEQUENCE: 2

```
Met Ser Ala Arg Thr Pro Leu Pro Thr Val Asn Glu Arg Asp Thr Glu
1               5                   10                  15

Asn His Thr Ser Val Asp Gly Tyr Thr Glu Pro His Ile Gln Pro Thr
            20                  25                  30

Lys Ser Ser Ser Arg Gln Asn Ile Pro Arg Cys Arg Asn Ser Ile Thr
        35                  40                  45

Ser Ala Thr Asp Glu Gln Pro His Ile Gly Asn Tyr Arg Leu Gln Lys
    50                  55                  60

Thr Ile Gly Lys Gly Asn Phe Ala Lys Val Lys Leu Ala Arg His Val
65                  70                  75                  80

Leu Thr Gly Arg Glu Val Ala Val Lys Ile Ile Asp Lys Thr Gln Leu
                85                  90                  95

Asn Pro Thr Ser Leu Gln Lys Leu Phe Arg Glu Val Arg Ile Met Lys
            100                 105                 110

Ile Leu Asn His Pro Asn Ile Val Lys Leu Phe Glu Val Ile Glu Thr
        115                 120                 125

Glu Lys Thr Leu Tyr Leu Val Met Glu Tyr Ala Ser Gly Gly Glu Val
    130                 135                 140

Phe Asp Tyr Leu Val Ala His Gly Arg Met Lys Glu Lys Glu Ala Arg
145                 150                 155                 160

Ala Lys Phe Arg Gln Ile Val Ser Ala Val Gln Tyr Cys His Gln Lys
                165                 170                 175

Tyr Ile Val His Arg Asp Leu Lys Ala Glu Asn Leu Leu Leu Asp Gly
            180                 185                 190

Asp Met Asn Ile Lys Ile Ala Asp Phe Gly Phe Ser Asn Glu Phe Thr
        195                 200                 205

Val Gly Asn Lys Leu Asp Thr Phe Cys Gly Ser Pro Pro Tyr Ala Ala
    210                 215                 220

Pro Glu Leu Phe Gln Gly Lys Lys Tyr Asp Gly Pro Glu Val Asp Val
225                 230                 235                 240

Trp Ser Leu Gly Val Ile Leu Tyr Thr Leu Val Ser Gly Ser Leu Pro
                245                 250                 255

Phe Asp Gly Gln Asn Leu Lys Glu Leu Arg Glu Arg Val Leu Arg Gly
            260                 265                 270
```

```
Lys Tyr Arg Ile Pro Phe Tyr Met Ser Thr Asp Cys Glu Asn Leu Leu
            275                 280                 285

Lys Lys Leu Leu Val Leu Asn Pro Ile Lys Arg Gly Ser Leu Glu Gln
290                     295                 300

Ile Met Lys Asp Arg Trp Met Asn Val Gly His Glu Glu Glu Leu
305                 310                 315                 320

Lys Pro Tyr Thr Glu Pro Asp Pro Asp Phe Asn Asp Thr Lys Arg Ile
                325                 330                 335

Asp Ile Met Val Thr Met Gly Phe Ala Arg Asp Glu Ile Asn Asp Ala
                340                 345                 350

Leu Ile Asn Gln Lys Tyr Asp Glu Val Met Ala Thr Tyr Ile Leu Leu
            355                 360                 365

Gly Arg Lys Pro Pro Glu Phe Glu Gly Gly Glu Ser Leu Ser Ser Gly
370                 375                 380

Asn Leu Cys Gln Arg Ser Arg Pro Ser Ser Asp Leu Asn Asn Ser Thr
385                 390                 395                 400

Leu Gln Ser Pro Ala His Leu Lys Val Gln Arg Ser Ile Ser Ala Asn
            405                 410                 415

Gln Lys Gln Arg Arg Phe Ser Asp His Ala Gly Pro Ser Ile Pro Pro
                420                 425                 430

Ala Val Ser Tyr Thr Lys Arg Pro Gln Ala Asn Ser Val Glu Ser Glu
            435                 440                 445

Gln Lys Glu Glu Trp Asp Lys Asp Val Ala Arg Lys Leu Gly Ser Thr
450                 455                 460

Thr Val Gly Ser Lys Ser Glu Met Thr Ala Ser Pro Leu Val Gly Pro
465                 470                 475                 480

Glu Arg Lys Lys Ser Ser Thr Ile Pro Ser Asn Asn Val Tyr Ser Gly
                485                 490                 495

Gly Ser Met Ala Arg Arg Asn Thr Tyr Val Cys Glu Arg Thr Thr Asp
            500                 505                 510

Arg Tyr Val Ala Leu Gln Asn Gly Lys Asp Ser Ser Leu Thr Glu Met
            515                 520                 525

Ser Val Ser Ser Ile Ser Ser Ala Gly Ser Ser Val Ala Ser Ala Val
530                 535                 540

Pro Ser Ala Arg Pro Arg His Gln Lys Ser Met Ser Thr Ser Gly His
545                 550                 555                 560

Pro Ile Lys Val Thr Leu Pro Thr Ile Lys Asp Gly Ser Glu Ala Tyr
                565                 570                 575

Arg Pro Gly Thr Thr Gln Arg Val Pro Ala Ala Ser Pro Ser Ala His
                580                 585                 590

Ser Ile Ser Thr Ala Thr Pro Asp Arg Thr Arg Phe Pro Arg Gly Ser
            595                 600                 605

Ser Ser Arg Ser Thr Phe His Gly Glu Gln Leu Arg Glu Arg Ser
            610                 615                 620

Val Ala Tyr Asn Gly Pro Pro Ala Ser Pro Ser His Glu Thr Gly Ala
625                 630                 635                 640

Phe Ala His Ala Arg Arg Gly Thr Ser Thr Gly Ile Ile Ser Lys Ile
                645                 650                 655

Thr Ser Lys Phe Val Arg Arg Asp Pro Ser Glu Gly Glu Ala Ser Gly
                660                 665                 670

Arg Thr Asp Thr Ser Arg Ser Thr Ser Gly Glu Pro Lys Glu Arg Asp
                675                 680                 685

Lys Glu Glu Gly Lys Asp Ser Lys Pro Arg Ser Leu Arg Phe Thr Trp
```

```
                  690             695             700
Ser Met Lys Thr Thr Ser Ser Met Asp Pro Asn Asp Met Met Arg Glu
705                 710                 715                 720

Ile Arg Lys Val Leu Asp Ala Asn Asn Cys Asp Tyr Glu Gln Lys Glu
                    725                 730                 735

Arg Phe Leu Leu Phe Cys Val His Gly Asp Ala Arg Gln Asp Ser Leu
                740                 745                 750

Val Gln Trp Glu Met Glu Val Cys Lys Leu Pro Arg Leu Ser Leu Asn
            755                 760                 765

Gly Val Arg Phe Lys Arg Ile Ser Gly Thr Ser Ile Ala Phe Lys Asn
        770                 775                 780

Ile Ala Ser Lys Ile Ala Asn Glu Leu Lys Leu
785                 790                 795
```

<210> SEQ ID NO 3
<211> LENGTH: 1262
<212> TYPE: DNA
<213> ORGANISM: Homo sapiens

<400> SEQUENCE: 3

```
cgcctctgac gccaccggct gggctccgcc atgagttcgg cgccggcctc aggctccgtg    60
cgcgcgcgct atcttgtgta cttccagtac gtgggcaccg actttaacgg ggtcgcggcc   120
gtcaggggca ctcagcgcgc cgtcggggtc cagaactacc tggaggaggc cgccgagcgg   180
ctgaattccg tggagccggt caggttcacc atctccagcc gcacggacgc cggggtccac   240
gccctgagca acgcggcgca cctggacgtc cagcgccgct caggccggcc gcccttcccg   300
cccgaggtcc tggccgaggc cctcaacaca cacctgcggc acccggccat cagggtcctg   360
cgggccttcc gagtgcccag cgacttccac gctcgtcacg cagccacgtc ccggacctac   420
ctgtaccgcc tggccactgg ctgtcaccgg cgtgatgagc tgccggtgtt tgaacgcaac   480
ctatgctgga ctctccccgg cagactgcctg gatatggtcg ccatgcagga agccgcccag   540
cacctcctcg gcacacacga cttcagcgcc ttccagtccg ctggcagccc ggtgccgagc   600
cccgtgcgaa cgctgcgccg ggtctccgtt tccccaggcc aagccagccc cttggtcacc   660
cccgaggaga gcaggaagct gcggttctgg aacctggagt ttgagagcca gtctttcctg   720
tatagacagg tacggaggat gacggctgtg ctggtggccg tggggctggg ggcttttggca   780
cctgcccagg tgaagacgat tctggagagc caagatcccc tgggcaagca ccagacacgt   840
gtagccccag cccacggctt attcctcaag tcagtgctgt acgggaacct cggtgctgcc   900
tcctgcaccc tgcaggggcc acagttcggg agccacggat gaccctggac actcaagcca   960
aagttaggcc acaccaggcc caaccctgtg ctggtcaagc cagggcagtc acagctgctt  1020
ggggcccaca gcactgctgc ctggtctcca cagtagcctc cctgcccggg tcccagcacc  1080
ctggatgccc gtctctgtcc caggcgggat ggggcacagt gcaggacaca gccatgtaca  1140
ccaagaagag agtaccaagt agtctttttgt tcagcttttta ctggaaactg ctgtctagga  1200
ccacctgccc taaccaggaa taaaggcaag acagcctgga aaaaaaaaa aaaaaaaa  1260
aa                                                                 1262
```

<210> SEQ ID NO 4
<211> LENGTH: 303
<212> TYPE: PRT
<213> ORGANISM: Homo sapiens

<400> SEQUENCE: 4

```
Met Ser Ser Ala Pro Ala Ser Gly Ser Val Arg Ala Arg Tyr Leu Val
1               5                   10                  15

Tyr Phe Gln Tyr Val Gly Thr Asp Phe Asn Gly Val Ala Ala Val Arg
            20                  25                  30

Gly Thr Gln Arg Ala Val Gly Val Gln Asn Tyr Leu Glu Glu Ala Ala
        35                  40                  45

Glu Arg Leu Asn Ser Val Glu Pro Val Arg Phe Thr Ile Ser Ser Arg
50                  55                  60

Thr Asp Ala Gly Val His Ala Leu Ser Asn Ala Ala His Leu Asp Val
65                  70                  75                  80

Gln Arg Arg Ser Gly Arg Pro Pro Phe Pro Glu Val Leu Ala Glu
                85                  90                  95

Ala Leu Asn Thr His Leu Arg His Pro Ala Ile Arg Val Leu Arg Ala
            100                 105                 110

Phe Arg Val Pro Ser Asp Phe His Ala Arg His Ala Ala Thr Ser Arg
        115                 120                 125

Thr Tyr Leu Tyr Arg Leu Ala Thr Gly Cys His Arg Arg Asp Glu Leu
130                 135                 140

Pro Val Phe Glu Arg Asn Leu Cys Trp Thr Leu Pro Ala Asp Cys Leu
145                 150                 155                 160

Asp Met Val Ala Met Gln Glu Ala Ala Gln His Leu Leu Gly Thr His
                165                 170                 175

Asp Phe Ser Ala Phe Gln Ser Ala Gly Ser Pro Val Pro Ser Pro Val
            180                 185                 190

Arg Thr Leu Arg Arg Val Ser Val Ser Pro Gly Gln Ala Ser Pro Leu
        195                 200                 205

Val Thr Pro Glu Glu Ser Arg Lys Leu Arg Phe Trp Asn Leu Glu Phe
210                 215                 220

Glu Ser Gln Ser Phe Leu Tyr Arg Gln Val Arg Arg Met Thr Ala Val
225                 230                 235                 240

Leu Val Ala Val Gly Leu Gly Ala Leu Ala Pro Ala Gln Val Lys Thr
                245                 250                 255

Ile Leu Glu Ser Gln Asp Pro Leu Gly Lys His Gln Thr Arg Val Ala
            260                 265                 270

Pro Ala His Gly Leu Phe Leu Lys Ser Val Leu Tyr Gly Asn Leu Gly
        275                 280                 285

Ala Ala Ser Cys Thr Leu Gln Gly Pro Gln Phe Gly Ser His Gly
290                 295                 300

<210> SEQ ID NO 5
<211> LENGTH: 6634
<212> TYPE: DNA
<213> ORGANISM: Homo sapiens

<400> SEQUENCE: 5
taaataatgg gaagcctttc aacttgaaac aggctcctag gagaccagaa gcagcagcct    60
ttcctgagct caggtaagag atcttaccct ctactgacac tgctcacgtt gttgtgagga   120
tcacctactt ctcctaatca tttacccagg tatgttcaag gtcacatcta aaggacccttt  180 ttccacgagg acaaaatctc tttgaggaca ataatcatc atgtttatct ttgtacttca    240
gtacctagca caacattcaa gacagcgggt gctcattaaa tgctcatcaa attgttagtt   300
caggacaact aacatcaatc tctacttaaa atgaattgat cacttgctct gtgctaagtg   360
tataaatcat agattattgt atttaaataa tcgatttaaa atcaaaacaa tttctgggtt   420
```

```
aagtttaatt atcaccattt tggggttaag aaaattaaac tcagaggtga gttgacttgt      480
ccaaggtcac atagaggtag ggtggccaac tcattccagt ttacctgtgg tttttccagt      540
tttaaaactg aaattttcgt atttcaggaa ccattccctg cccccccaacc tcagtcctgg     600 gtaaactgga atgacccaca tcaatggaaa ctagtaaagc gaggatttat ttggacccag      660
ttctcttgtc tccaaaccca gagtcctctt tgattctttt gggtttggtt tgcttttttc      720
cttttcctac atttgacagt atctcgagtg gtcacaaatg taaaaatgt ctagcatatt       780 gcctggcata taggaaaaat tcagtaagtg ataatgatta tcagtgctgt gccaagctat      840
ggagccagcc atatatatat ggatgtgtgc atatatatat atgatgtgtg tgtatatata      900
tatgtcttta taaattttat gtatttattt ctttcaaaaa tattaaagta tttgagaaaa      960
ttgaaaaatt aaaagtagg tttattacga ctcatgactt taagtttaaa tattttattt      1020
ctgccccaaa caaatttat tataatttta ctgtcctggt tttaagggaa ggaaactcat      1080
caataatatt ttcatcatat gcttttgaga aacaaagtta accattaaga atgaaacatg      1140
aaaacatgtg aatagtggta caaattttc cttttgcttc aatatggctc agcatggcac       1200
tgtcgaattt tgtctttata taaaattttg atattttgtt tgtcataagc ttttttaattc     1260 attttatat tgcactaaaa tatttttatc ttgatgactg aggtttttta gtgctcccctt      1320 aaattttgca cctaaaatga gtgcctcaat tgttttaccc taacctcagc ccattattat      1380
tttatcttaa aactcagcaa acaccctaac ctgctctctt actgaggagg ctcgcccaag      1440
aataaatgag ttccgtcatt gccttttcttc tctgacttt gggaccattt gcttggtcta      1500
ggacctgagt tgcaggtcca ggaaagcgtg tactctcgaa tccacccagg agtgcctgac      1560
tacagtcctc ctgcagaggg cgctgtggag tcccagacac gagtgttagg tggaatcggg      1620
ctgattgccc atcacgtctt gccttctcct ggcagtaggc ttgttatgaa atcattgact      1680
ttctatttgc ctctgggct taagcgaatc tgttaccctc aaataaccta tctgatctca      1740
gacaaatgcc aaacagagct cagtttctct gccctgtggg tggccataaa atccagacaa      1800 tttccccta ggtgttttcg atggcgcagc cacagcttct gtgagattcg atttctcccc       1860
agttcccctg tgggtctgag gggaccagaa gggtgagcta cgttggcttt ctggaagggg      1920
aggctatatg cgtcaattcc ccaaaacaag ttttgacatt tccctgaaa tgtcattctc      1980 tatctattca ctgcaagtgc ctgctgttcc aggcctacc tgctgggcac taacggcgga      2040
gccaggatgg ggacagaata aaggagccac gacctgtgcc accaactcgc actcagactc      2100
tgaactcaga cctgaaatct tctcttcacg ggaggcttgg cagttttct tagtaagttg      2160 cgtggatggg ccacactgtc tgaggccaga taaggctgtt ctcttcccct gacccccac      2220 ccctcaccc gtggacactt ggaggagggg aaactcagta agtcatgctc tcttctttga      2280
attcctagct cctgtggtct ccagatttca ggcctaagat gaaagcctct agtcttgcct      2340
tcagccttct ctctgctgcg ttttatctcc tatggactcc ttccactgga ctgaagacac      2400
tcaatttggg aagctgtgtg atcgccacaa accttcagga aatacgaaat ggattttctg      2460
agatacgggg cagtgtggta cgtaagcggg tatctacctc tcctgaaagc cttttctctt      2520
ccttccttgt ccgtttctct ttcctggcag tactggcagt gtaatcataa aaagaggcag      2580
gctggggatt ccttacccgg gggatgtatt ccaaagaaat aactgtagtt caaatattta      2640
aaatgttttg ggaaaggaca cctcccacta gttcttggca gggagtggat gagaagtctt      2700
gatattgaag accctggcag caggcactga ctcatccttg cttgttttgt cttcttctgt      2760
```

```
ttagcaagcc aaagatggaa acattgacat cagaatctta aggaggactg agtctttgca    2820
agacacaaag gtatgtgctt ggcccagaca aactctggga ggaggagtgg agtgggagca    2880
tctccatcac cctggtcttg tctctgctct cccctttccc ctcaccaata tacctgtggt    2940
tttttgcagc ctgcgaatcg atgctgcctc ctgcgccatt tgctaagact ctatctggac    3000
agggtattta aaaactacca gacccctgac cattatactc tccggaagat cagcagcctc    3060
gccaattcct ttcttaccat caagaaggac ctccggctct gtgtgagtgt gggtcttggg    3120
tgacaggatg catctcagca cacagcttca atggcttagc aactaaactc tctttcctac    3180
ctccattta a tggatggaga aactgagtcc aaaagttcta ataatctgtg ttgagacatg    3240
tgactaggta ataagaactc agttttattg acttttcggt atatgctcta ggcaaaaagt    3300
actttgcaaa gtctaaagaa ctataagatg ctaactattt gatattaatg ataactctgt    3360
tgtctttgaa attatacttt ttctgtaggt gaggtatcct acagtatatt agtgcgtcct    3420
ctgtctaggc agtcaattag tagaccattg agcttgacct cagaatatag tctgaatagg    3480
acctaggaat tcaattcttt tttttttttt tctcaatggg ggctcaaaga gctctgggat    3540
agagctccta gactacagct gggggttgtg gggaggccag atggggtacg gggatggcaa    3600
atgccttcag tactgcctgc ctattttctaa aaaagaagtg atgagttcca tgtttgagcc    3660
taaaaggtgg cttcctctcc tagctgatga tgaacttaat gattccaaat gtgaggtctg    3720
aaagagcttt tctataggaa taagcatcct cagggttgtg ggtgaaagag tagagttttct    3780
acctgcttca tgtcaatggc aaaaaatcag aatctgtaat ataatctatt attctttggg    3840
tcctttcag catgcccaca tgacatgcca ttgtggggag gaagcaatga agaaatacag    3900
ccagattctg agtcactttg aaaaggtata tgcgactttg gcattgattg ggatgggtgt    3960
gttttaagaa ctgagatcat aggtaggtgg gatggttatt cactgttaga catcctgtag    4020
ccttcaggtt catagccctc tgaaatcatg aggaccagcc cttgctttaa cccaggggac    4080
acccatccag gctctagagg agtaccctct ctgggtgatg tctctggaaat ggaaagggaa    4140
tggccatgat tccatcaagt cactacagtg acatctggat cttttagctg cacaaaccag    4200
aggcaatagt tttacaatgt tcacacactt ctatgtacct ttgaaaacac tcacaatttc    4260
acacacacac ccatgccatt caatttctca ccttcacacc ttctcatgtc tgccaggaag    4320
gcctggattt cactcctcac tgactaaatc ctactcatcc tttaaagact cagcctgggc    4380
atcactttca ggaaggtgct ggctccttct ctcagagtta gatgcctccc acatcatctt    4440
gtaggaattt catcccttta ttcaccacac tacattttag ttgcctgttt ttgccagtct    4500
cctcactcaa ctgtggatag ggattgtgcc attcaccttt tcatccctaa ccatcagcta    4560
ggtgattggc acaatcaata tctgttcaac tgatgtgtgc accgtaggca accctacac    4620
acacacacag gcacgtgcac acacacacac acacacgttt cttaaagaaa atagcttgat    4680
tattttgatc tctgtgattc aagagtctta agtagcagtt ttacttctgc tacccccttg    4740
cacctcagtt tctgtacata agaccagggt gatgaactca atgatttccc ttccttgtgt    4800
gatatcttga gattctataa cttctttaag tgcttcatct tgaaaagaat gctctgctta    4860
caattgtcag cagacctatc cataaaagag ataggtcctg gagcaaatgc tgtctcatga    4920
attgctaacc acatgggtgt gtgtctcttt cagctggaac ctcaggcagc agttgtgaag    4980
gctttggggg aactagacat tcttctgcaa tggatggagg agacagaata ggaggaaagt    5040
gatgctgctg ctaagaatat tcgaggtcaa gagctccagt cttcaatacc tgcagaggag    5100
gcatgacccc aaaccaccat ctctttactg tactagtctt gtgctggtca cagtgtatct    5160
```

```
tatttatgca ttacttgctt ccttgcatga ttgtctttat gcatccccaa tcttaattga    5220
gaccatactt gtataagatt tttgtaatat ctttctgcta ttggatatat ttattagtta    5280
atatatttat ttatttttg  ctatttaatg tatttatttt tttacttgga catgaaactt    5340
taaaaaaatt cacagattat atttataacc tgactagagc aggtgatgta tttttataca    5400
gtaaaaaaaa aaaaccttgt aaattctaga agagtggcta gggggggttat tcatttgtat    5460 tcaactaagg acatatttac tcatgctgat gctctgtgag atatttgaaa ttgaaccaat    5520
gactacttag gatgggttgt ggaataagtt ttgatgtgga attgcacatc taccttacaa    5580
ttactgacca tccccagtag actccccagt cccataattg tgtatcttcc agccaggaat    5640
cctacacggc cagcatgtat ttctacaaat aaagttttct ttgcataaca tctgcttgga    5700
gtttgcaaat gtttcaagag cagagaccat gttgaggata agtttgaatc tcatttcacc    5760
ccaggtcctc ttgctccttt gaggaagaag atgtaggaac ctcgatcttc tctctcctgc    5820
agatttcatc ctcagctcta tctcctaatt catactgctc tgaccccacg actgccctcc    5880
tctcaaaagg actgtgacag agtgaggggc ttcagccatc tctgctttcg cctcattggc    5940
ttggagcact gccctttcta tacctctgtt ttctttctca ccccataccc ttgcaagaca    6000
aattacaatg ggcatgaggc gctattataa aggttaaaaa cacacaggtg caaagtgtag    6060
gtctagagtc ttgcccagac aggtgtatga gccccttttt gaggcccttc catttttggat    6120 tctgtccagc ctcagagttt aggttgttac cagatcaagt ccttatcttt gtgtccaact    6180
attaagtcag tgtttctttt ccaggccccc ttcaggttga gtgtccctgg acactgagga    6240
gccagagttc tggcctgggc tggttccttc cttcttcccc cacctcactc tgaagcgcac    6300 ccccaatta  gttgcttagt tttctcagtc tcagaaacaa cagtctcagg ctgattccct    6360
gggtcctaaa gataactctc cttactgctt taatttctac tccctgttct tagcctgggc    6420
cctgatatag tttcaatgac tttaactttt gataactctc attatacaag taacagctgc    6480
ccaacagaaa agaaatttg  gaagaaaaca gaaatataaa gaagaaaatt aaaatcaccc    6540
ataatctcac caccctcaga caaccacttt taaacattta tgcttatttt ttccagatat    6600
tttttgatgg gttcaaatca tgactcagct ctca                                6634
```

<210> SEQ ID NO 6
<211> LENGTH: 176
<212> TYPE: PRT
<213> ORGANISM: Homo sapiens

<400> SEQUENCE: 6

Met Lys Ala Ser Ser Leu Ala Phe Ser Leu Leu Ser Ala Ala Phe Tyr
1               5                   10                  15

Leu Leu Trp Thr Pro Ser Thr Gly Leu Lys Thr Leu Asn Leu Gly Ser
            20                  25                  30

Cys Val Ile Ala Thr Asn Leu Gln Glu Ile Arg Asn Gly Phe Ser Glu
        35                  40                  45

Ile Arg Gly Ser Val Gln Ala Lys Asp Gly Asn Ile Asp Ile Arg Ile
    50                  55                  60

Leu Arg Arg Thr Glu Ser Leu Gln Asp Thr Lys Pro Ala Asn Arg Cys
65                  70                  75                  80

Cys Leu Leu Arg His Leu Leu Arg Leu Tyr Leu Asp Arg Val Phe Lys
                85                  90                  95

Asn Tyr Gln Thr Pro Asp His Tyr Thr Leu Arg Lys Ile Ser Ser Leu
            100                 105                 110

```
Ala Asn Ser Phe Leu Thr Ile Lys Lys Asp Leu Arg Leu Cys His Ala
        115                 120                 125

His Met Thr Cys His Cys Gly Glu Glu Ala Met Lys Lys Tyr Ser Gln
    130                 135                 140

Ile Leu Ser His Phe Glu Lys Leu Glu Pro Gln Ala Ala Val Val Lys
145                 150                 155                 160

Ala Leu Gly Glu Leu Asp Ile Leu Leu Gln Trp Met Glu Glu Thr Glu
                165                 170                 175

<210> SEQ ID NO 7
<211> LENGTH: 98
<212> TYPE: PRT
<213> ORGANISM: Homo sapiens

<400> SEQUENCE: 7

Met Ala Leu Leu Leu Ala Leu Ser Leu Leu Val Leu Trp Thr Ser Pro
1               5                   10                  15

Ala Pro Thr Leu Ser Gly Thr Asn Asp Ala Glu Asp Cys Cys Leu Ser
            20                  25                  30

Val Thr Gln Lys Pro Ile Pro Gly Tyr Ile Val Arg Asn Phe His Tyr
        35                  40                  45

Leu Leu Ile Lys Asp Gly Cys Arg Val Pro Ala Val Val Phe Thr Thr
    50                  55                  60

Leu Arg Gly Arg Gln Leu Cys Ala Pro Pro Asp Gln Pro Trp Val Glu
65                  70                  75                  80

Arg Ile Ile Gln Arg Leu Gln Arg Thr Ser Ala Lys Met Lys Arg Arg
                85                  90                  95

Ser Ser
```

EARLY STAGE PARKINSON'S DISEASE DIAGNOSTIC KITS AND METHODS

CROSS-REFERENCE TO RELATED APPLICATIONS

This application is a divisional of, and claims priority to, U.S. application Ser. No. 15/041,573, now issued as U.S. Pat. No. 10,436,801, which claims priority under 35 U.S.C. § 119(e) to U.S. Provisional Application No. 62/114,971, filed Feb. 11, 2015, all of which are incorporated herein by reference in their entireties.

FIELD OF THE INVENTION

This invention relates to the diagnosis of early-stage Parkinson's disease (PD) using autoantibodies as blood-based biomarkers.

BACKGROUND OF THE INVENTION

PD is the second most common neurodegenerative disease worldwide and affects more than one percent of people older than sixty years of age and roughly four percent of those older than 85 (de Lau et al. *The Lancet Neurology* 5, 525-535 (2006)). Currently, there is no simple and reliable diagnostic test for PD. It remains essentially a clinical diagnosis, subject to variations in patient presentation and physician awareness. Upon post-mortem examination, it has been estimated that only 80% of patients clinically diagnosed with PD have typical post-mortem neuropathological changes (Hughes et al. *Archives of neurology* 50, 140-148 (1993)). Even in subjects with an apparently positive response to dopaminergic medication, a clinical diagnosis of PD can have relatively poor accuracy (Adler et al. *Neurology* 83, 406-412 (2014)). Results are far worse for very Early-Stage PD subjects (Adler et al. *Neurology* 82, 858-864 (2014)). Neuroimaging approaches such as DaT scanning have some utility, but are expensive, invasive, and not very specific. Detection of biomarkers in the cerebrospinal fluid (CSF) or blood, presumably associated with PD pathogenesis, such as alpha-synuclein or DJ-1, has so far failed to yield consistent results (Hong et al. *Brain: a journal of neurology* 133, 713-726 (2010), Gerlach et al. *Journal of neural transmission* 119, 39-52 (2012), van Dijk et al. *European journal of neurology: the official journal of the European Federation of Neurological Societies* 21, 388-394 (2014), Mollenhauer et al. *Experimental neurology* 213, 315-325 (2008), and Aerts et al. *Neurobiology of aging* 33, 430 e431-433 (2012). Thus, there remains a great need for an accurate, inexpensive, and noninvasive test that can detect PD in its earliest stages.

SUMMARY OF INVENTION

This invention relates to a diagnosis of Early-Stage PD using autoantibodies as blood-based biomarkers.

In some embodiments, the present invention provides a method of identifying a subject that has or is at risk of developing Early-Stage PD comprising obtaining an immunoglobulin-containing biological sample from the subject, performing an assay to determine the presence or absence of at least one Early-Stage PD autoantibody biomarker in the biological sample, and identifying the subject who has or is at risk for developing Early-Stage PD if at least one Early-Stage PD autoantibody biomarker is present. Each of the Early-Stage PD autoantibody biomarkers is an autoantibody that specifically binds to at least one target selected from the group consisting of the target antigens listed in Table 1.

In some embodiments, the assay can be performed by a process comprising contacting the immunoglobulin-containing sample with at least one target antigen or an epitope thereof under conditions that allow formation of an immunocomplex between (i) the antigen or an epitope thereof and (ii) the autoantibody biomarker, and detecting the presence or absence of the immunocomplex. The presence of the immunocomplex is indicative of the presence of the biomarker and the disease and wherein the absence of an immunocomplex is indicative of the absence of the biomarker and lack of the disease. The antigen can be selected from the group listed in Table 1 or FIG. 4, and antigenic fragments thereof.

In another embodiment, the present invention provides a method of generating a patient-specific Early-Stage PD autoantibody biomarker profile comprising obtaining an immunoglobulin-containing biological sample from a patient, performing an assay to determine the presence or absence of at least one Early-Stage PD autoantibody biomarkers in the biological sample, and generating a patient-specific Early-Stage PD autoantibody biomarker profile of the Early-Stage PD autoantibody biomarker(s) present in the sample. In another embodiment, the methods of the present claims can further be employed to monitor therapeutic outcome and the progress of a subjects undergoing PD treatment.

In one embodiment, the assay is performed to determine presence or absence of four or more Early-Stage PD autoantibody biomarkers in the biological sample. For example, the assay can be performed to determine the presence or absence of the following four Early-Stage PD autoantibody biomarkers/autoantibodies that specifically bind to Serine/threonine-protein kinase MARK1, tRNA pseudouridine synthase-like 1 (PUSL1), Interleukin-20 (IL20), and C—C motif chemokine 19 (CCL19).

In some embodiments, the immunoglobulin-containing biological sample can be serum, plasma, whole blood, CSF, saliva, or sputum.

The target antigen or an epitope thereof can be attached to a substrate. The one or more target antigens or antigenic fragments/epitopes thereof for the one or more Early-Stage PD autoantibody biomarkers can be in the form of an array, such as a microarray. In one embodiment, the microarray can include a substrate on which the target antigens listed in Table 1 or FIG. 4 or antigenic fragments/epitopes thereof are immobilized. In some embodiments, the Microarray can be prepared on a glass surfaces with a variety of coatings including but not limited to nitrocellulose, FAST™, Full-Moon™, SuperEpoxy™, SuperAldehyde™, SuperNHS™, Ni-NTA, PATH, Nextirion, Nexterion H thin film, epoxysilane or aldehydesilane or other similar coatings known to those of ordinary skill in the art. In some embodiments, the substrate can be a nitrocellulose-coated glass slide.

In some embodiments, the invention allows one to discriminate between Early-Stage PD and Mild-Moderate PD. In other embodiments, the invention allows one to discriminate between Early-Stage PD and a non-PD condition. Examples of the non-PD condition include Alzheimer's disease, multiple sclerosis, and cancer. In yet other embodiments, the presence of at least one autoantibody biomarker in a sample from a subject is capable of forming at least a part of a basis of a diagnosis of the subject as having Early-Stage PD.

In a second aspect, the invention provides a conjugate having (i) one or more antigens that are specific for one or more Early Stage PD biomarkers, and (ii) a substrate on which the one or more antigens are immobilized. Examples of the antigens include those selected from the group consisting of the target antigens listed in Table 1 and antigenic fragments thereof. For example, the substrate can have immobilized thereon a plurality of individually addressable antigens that are specific for the Early-Stage PD biomarkers respectively. The substrate can be a slide or a bead. In one embodiment, the antigens can be those selected from the group consisting of the proteins listed in FIG. 4 and antigenic fragments thereof. In another embodiment, the conjugate can further comprise the one or more Early-Stage PD biomarkers or one or more detection agents, such as a secondary antibodies and indicator reagents as described below.

In a third aspect, the invention features a microarray comprising a plurality of conjugates described above. In at least one embodiment, such microarrays may be used to identify or screen candidate therapeutic regimens and/or therapeutic agents suitable for treatment of Early-Stage or Mild and Moderate Stage PD. In at least one embodiment, agents that decrease the level of autoantibody biomarkers, inhibiting or reducing the activity of the Early-Stage PD biomarkers may be used as therapeutic agents to treat Early-Stage PD.

In a fourth aspect, the invention provides a kit comprising (i) one or more antigens that are specific for one or more Early-Stage PD biomarkers, and (ii) reagents for determining binding of the antigens to the Early-Stage PD biomarkers. The antigens can be selected from the group consisting of the proteins listed in Table 1 and antigenic fragments thereof. The one or more antigens or antigenic fragments thereof can be immobilized on a substrate.

In a fifth aspect, the invention provides a plurality of immunocomplexes, each complex comprising (i) an Early-Stage PD autoantibody biomarker, said autoantibody specifically binding to a target antigen selected from the group consisting of the proteins listed in Table 1; (ii) said antigen or an antigenic fragment thereof, and (iii) a detection agent.

In some embodiments, the assay performed to determine the presence or absence of at least one Early-Stage PD autoantibody biomarker uses at least one (1) target antigen or antigenic fragments thereof.

In some embodiments, the assay performed to determine the presence or absence of at least one Early-Stage PD autoantibody biomarker uses at least four (4) target antigens or antigenic fragments thereof.

In some embodiments, the assay performed to determine the presence or absence of at least one Early-Stage PD autoantibody biomarker uses at least five (5) target antigens or antigenic fragments thereof.

In some embodiments, the assay performed to determine the presence or absence of at least one Early-Stage PD autoantibody biomarker uses at least ten (10) target antigens or antigenic fragments thereof.

In some embodiments, the assay performed to determine the presence or absence of at least one Early-Stage PD autoantibody biomarker uses at least twenty-five (25) target antigens or antigenic fragments thereof.

In some embodiments, the assay performed to determine the presence or absence of at least one Early-Stage PD autoantibody biomarker uses at least fifty (50) target antigens or antigenic fragments thereof.

In some embodiments, the assay performed to determine the presence or absence of at least one Early-Stage PD autoantibody biomarker uses between one (1) and five (5) (inclusive) target antigens or antigenic fragments thereof.

In some embodiments, the assay performed to determine the presence or absence of at least one Early-Stage PD autoantibody biomarker uses between one (1) and ten (10) (inclusive) target antigens or antigenic fragments thereof.

In some embodiments, the assay performed to determine the presence or absence of at least one Early-Stage PD autoantibody biomarker uses between five (5) and ten (10) (inclusive) target antigens or antigenic fragments thereof.

In some embodiments, the assay performed to determine the presence or absence of at least one Early-Stage PD autoantibody biomarker uses between one (1) and twenty five (25) (inclusive) target antigens or antigenic fragments thereof.

In some embodiments, the assay performed to determine the presence or absence of at least one Early-Stage PD autoantibody biomarker uses between one (1) and twenty five (25) (inclusive) target antigens or antigenic fragments thereof.

In some embodiments, the assay performed to determine the presence or absence of at least one Early-Stage PD autoantibody biomarker uses between one (1) and fifty (50) (inclusive) target antigens or antigenic fragments thereof.

In some embodiments, the assay performed to determine the presence or absence of at least one Early-Stage PD autoantibody biomarker uses at least one target antigen or antigenic fragments thereof from Table 1.

In some embodiments, the assay performed to determine the presence or absence of at least one Early-Stage PD autoantibody biomarker uses at least four (4) target antigens from Table 1 or antigenic fragments thereof.

In some embodiments, the assay performed to determine the presence or absence of at least one Early-Stage PD autoantibody biomarker uses at least five (5) target antigens from Table 1 or antigenic fragments thereof.

In some embodiments, the assay performed to determine the presence or absence of at least one Early-Stage PD autoantibody biomarker uses at least ten (10) target antigens from Table 1 or antigenic fragments thereof.

In some embodiments, the assay performed to determine the presence or absence of at least one Early-Stage PD autoantibody biomarker uses at least twenty-five (25) target antigens from Table 1 or antigenic fragments thereof.

In some embodiments, the assay performed to determine the presence or absence of at least one Early-Stage PD autoantibody biomarker uses at least fifty (50) target antigens from Table 1 or antigenic fragments thereof.

In some embodiments, the assay performed to determine the presence or absence of at least one Early-Stage PD autoantibody biomarker uses between one (1) and five (5) (inclusive) target antigens from Table 1 or antigenic fragments thereof.

In some embodiments, the assay performed to determine the presence or absence of at least one Early-Stage PD autoantibody biomarker uses between one (1) and ten (10) (inclusive) target antigens from Table 1 or antigenic fragments thereof.

In some embodiments, the assay performed to determine the presence or absence of at least one Early-Stage PD autoantibody biomarker uses between five (5) and ten (10) (inclusive) target antigens from Table 1 or antigenic fragments thereof.

In some embodiments, the assay performed to determine the presence or absence of at least one Early-Stage PD autoantibody biomarker uses between one (1) and twenty five (25) (inclusive) target antigens from Table 1 or antigenic fragments thereof.

In some embodiments, the assay performed to determine the presence or absence of at least one Early-Stage PD autoantibody biomarker uses between ten (10) and twenty five (25) (inclusive) target antigens from Table 1 or antigenic fragments thereof.

In some embodiments, the assay performed to determine the presence or absence of at least one Early-Stage PD autoantibody biomarker uses between one (1) and fifty (50) (inclusive) target antigens from Table 1 or antigenic fragments thereof.

In another embodiment, the present invention provides a substrate on which at least one target antigen or antigenic fragment thereof that is specific for at least one Early-Stage PD autoantibody biomarker is immobilized.

In some embodiments, at least four (4) target antigens or antigenic fragments thereof are immobilized on the substrate.

In some embodiments, at least five (5) target antigens or antigenic fragments thereof are immobilized on the substrate.

In some embodiments, at least ten (10) target antigens or antigenic fragments thereof are immobilized on the substrate.

In some embodiments, at least twenty-five (25) target antigens or antigenic fragments thereof are immobilized on the substrate.

In some embodiments, at least fifty (50) target antigens or antigenic fragments thereof are immobilized on the substrate.

In some embodiments, between one (1) and five (5) (inclusive) target antigens or antigenic fragments thereof are immobilized on the substrate.

In some embodiments, between one (1) and ten (10) (inclusive) target antigens or antigenic fragments thereof are immobilized on the substrate.

In some embodiments, between five (5) and ten (10) (inclusive) target antigens or antigenic fragments thereof are immobilized on the substrate.

In some embodiments, between five (5) and twenty-five (25) (inclusive) target antigens or antigenic fragments thereof are immobilized on the substrate.

In some embodiments, between ten (10) and twenty-five (25) (inclusive) target antigens or antigenic fragments thereof are immobilized on the substrate.

In some embodiments, between one (1) and twenty-five (25) (inclusive) target antigens or antigenic fragments thereof are immobilized on the substrate.

In some embodiments, between one (1) and fifty (50) (inclusive) target antigens or antigenic fragments thereof are immobilized on the substrate.

In some embodiments, at least one target antigen or antigenic fragments thereof from Table 1 is immobilized on the substrate.

In some embodiments, at least four (4) target antigens from Table 1 or antigenic fragments thereof are immobilized on the substrate.

In some embodiments, at least five (5) target antigens from Table 1 or antigenic fragments thereof are immobilized on the substrate.

In some embodiments, at least ten (10) target antigens from Table 1 or antigenic fragments thereof are immobilized on the substrate.

In some embodiments, at least twenty-five (25) target antigens from Table 1 or antigenic fragments thereof are immobilized on the substrate.

In some embodiments, at least fifty (50) target antigens from Table 1 or antigenic fragments thereof are immobilized on the substrate.

In some embodiments, between one (1) and five (5) (inclusive) target antigens from Table 1 or antigenic fragments thereof are immobilized on the substrate.

In some embodiments, between one (1) and ten (10) (inclusive) target antigens from Table 1 or antigenic fragments thereof are immobilized on the substrate.

In some embodiments, between five (5) and ten (10) (inclusive) target antigens from Table 1 or antigenic fragments thereof are immobilized on the substrate.

In some embodiments, between five (5) and twenty-five (25) (inclusive) target antigens from Table 1 or antigenic fragments thereof are immobilized on the substrate.

In some embodiments, between ten (10) and twenty-five (25) (inclusive) target antigens from Table 1 or antigenic fragments thereof are immobilized on the substrate.

In some embodiments, between one (1) and twenty-five (25) (inclusive) target antigens from Table 1 or antigenic fragments thereof are immobilized on the substrate.

In some embodiments, between one (1) and fifty (50) (inclusive) target antigens from Table 1 or antigenic fragments thereof are immobilized on the substrate.

In a further embodiment, the present invention provides a kit for detecting Early-Stage PD autoantibody biomarkers.

In some embodiments, the kit contains at least one target antigen or antigenic fragments thereof.

In some embodiments, the kit contains at least five (5) target antigens or antigenic fragments thereof.

In some embodiments, the kit contains at least twenty-five (25) target antigens or antigenic fragments thereof.

In some embodiments, the kit contains at least fifty (50) target antigens or antigenic fragments thereof.

In some embodiments, the kit contains between one (1) and five (5) (inclusive) target antigens or antigenic fragments thereof.

In some embodiments, the kit contains between one (1) and ten (10) (inclusive) target antigens or antigenic fragments thereof.

In some embodiments, the kit contains between one (1) and twenty five (25) (inclusive) target antigens or antigenic fragments thereof.

In some embodiments, the kit contains between five (5) and ten (10) (inclusive) target antigens or antigenic fragments thereof.

In some embodiments, the kit contains between five (5) and twenty-five (25) (inclusive) target antigens or antigenic fragments thereof.

In some embodiments, the kit contains between ten (10) and twenty-five (25) (inclusive) target antigens or antigenic fragments thereof.

In some embodiments, the kit contains between one (1) and twenty-five (25) (inclusive) target antigens or antigenic fragments thereof.

In some embodiments, the kit contains at least one target antigen from Table 1 or antigenic fragments thereof.

In some embodiments, the kit contains at least four (4) target antigens from Table 1 or antigenic fragments thereof.

In some embodiments, the kit contains at least five (5) target antigens from Table 1 or antigenic fragments thereof.

In some embodiments, the kit contains at least twenty-five (25) target antigens from Table 1 or antigenic fragments thereof.

In some embodiments, the kit contains at least fifty (50) target antigens from Table 1 or antigenic fragments thereof.

In some embodiments, the kit contains between one (1) and five (5) (inclusive) target antigens from Table 1 or antigenic fragments thereof.

In some embodiments, the kit contains between one (1) and ten (10) (inclusive) target antigens from Table 1 or antigenic fragments thereof.

In some embodiments, the kit contains between five (5) and ten (10) (inclusive) target antigens from Table 1 or antigenic fragments thereof.

In some embodiments, the kit contains between five (5) and twenty-five (25) (inclusive) target antigens from Table 1 or antigenic fragments thereof.

In some embodiments, the kit contains between ten (10) and twenty-five (25) (inclusive) target antigens from Table 1 or antigenic fragments thereof.

In some embodiments, the kit contains between one (1) and twenty-five (25) (inclusive) target antigens from Table 1 or antigenic fragments thereof. In some embodiments, the present invention provides for diagnostic systems for detecting an Early-Stage PD autoantibody biomarker in a subject who has or is suffering from or is at risk of developing Parkinson's Disease, the system comprising (a) obtaining an immunoglobulin-containing biological sample from the subject, (b) conducting an immunoassay to detect at least four target antigens or antigenic fragments thereof specific for Early-Stage PD, (c) detecting the presence or absence of an immunocomplex, wherein the presence of an immunocomplex is indicative of the presence of the Early-Stage PD autoantibody biomarker in said subject and the presence of the disease and wherein the absence of an immunocomplex is indicative of the absence of the Early Stage PD autoantibody biomarkers and thus lack of the disease, (d) generating a report identifying subjects having Early Stage PD or are at the risk of developing Early Stage PD, and (e) optimizing the treatment plan in subjects in need thereof, by instituting a suitable anti Parkinson's therapeutic regimen.

In another aspect of the present invention, methods of treating patients with Early Stage PD or is at risk of developing early stage PD or are suffering from the same are described.

The details of one or more embodiments of the invention are set forth in the description below. Other features, objectives, and advantages of the invention will be apparent from the description and from the claims.

BRIEF DESCRIPTION OF THE DRAWINGS

FIG. 2A shows comparison of Early-Stage PD (n=103) vs. age-matched controls (n=111) using a panel of 50 (dark black line) or 4 (grey line) biomarkers show that these biomarker panels can be used to detect Early-Stage PD with relatively high overall accuracy. The dashed line represents the line of no discrimination, meaning that the diagnostic would have no utility if the plot followed this line. The ROC AUC, sensitivity, and specificity values for the 50 and 4 biomarkers are shown in Table 3.

FIG. 2B is a ROC curve diagram showing assessment of autoantibody biomarkers for monitoring PD progression and staging. Comparison of Early-Stage PD (n=103) vs. mild-moderate PD (n=29) using a panel of 50 (dark black line) or 4 (grey line) biomarkers (which are substantially overlapping) showing that autoantibody biomarkers can be used to accurately distinguish different stages of PD progression. The ROC AUC, sensitivity, and specificity values for the 50 and 4 biomarkers are shown in Table 3.

DETAILED DESCRIPTION OF THE INVENTION

Figure 1:
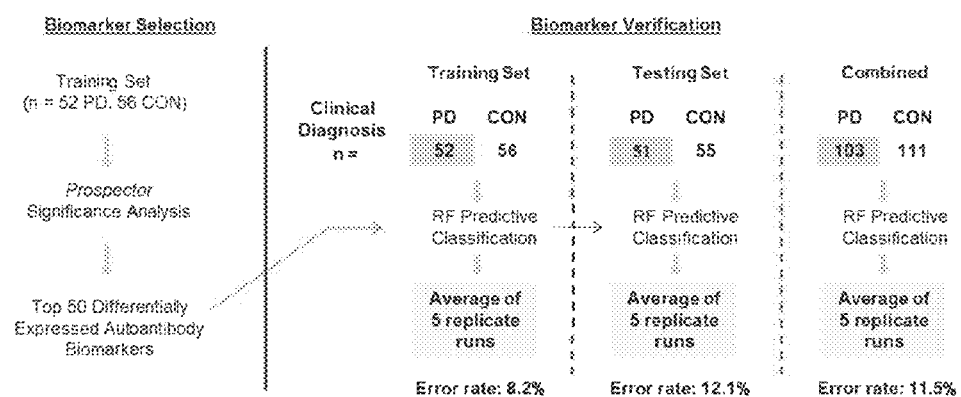
FIG. 1 is a diagram showing the biomarker selection and Training/Testing Set analysis strategy. The total sample pool (n=214) was randomly split into two groups: Training Set and Testing Set. Prospector statistical analysis was performed on the Training Set to identify the top 50 most differentially expressed autoantibody classifiers in early stage PD samples compared to controls. The diagnostic accuracy of these selected biomarkers was tested by using Random Forest to predict sample classification in the Training Set, Testing Set, and both sets combined.

This invention is based, at least in part, on unexpected discoveries that a number of panels of autoantibodies can be used for an accurate, inexpensive, and noninvasive test to detect PD in its earliest stages.

As PD begins, the area of the brain which is affected is rather localized. For example, the substantia nigra starts to deteriorate. The body's immune system quickly determines the type of tissue which is being damaged and produces autoantibodies to clear away that debris. Accordingly, this stage is the time that the autoantibodies/biomarkers disclosed in this invention are useful, and as used herein the term "Early-Stage PD" refers to this stage of PD. At this stage, a subject or patient does not show at least one, two, three, four, or all of the following typical PD symptoms: slowness of movement (bradykinesia), rigidity, resting tremor, postural instability, and response to levodopa. To that end, the subject or patient's Hoehn and Yahr scale score is no greater than 3, e.g., no greater than 2.5, 2.0, 1.5, or 1.0.

Later as the disease advances, inflammation becomes more widespread and sections of the brain which were not initially involved in the disease mechanism begin to die resulting in many different autoantibodies being present and thereby increasing the complexity of that portion of the autoantibody profile linked to the disease. The later stage autoantibody pattern might be, however, a good indicator of whether or how fast the disease is progressing.

Early-Stage PD Autoantibody Biomarkers

As used herein "Early-Stage PD autoantibody biomarkers" or "autoantibody biomarkers" refer to antibodies, including, for example, autoantibodies which specifically bind to target antigens and may serve as diagnostic indicators that can be used to differentiate Early-Stage PD from control subjects. As used herein, the term "Early-Stage PD autoantibody biomarkers" as defined herein include compositions that meet at least one of the following three criteria: i) is capable of detecting and specifically binding to at least one target antigen of the present invention; ii) is capable of serving as a diagnostic indicator of Early-Stage Parkinson's Disease, e.g. can be used to differentiate Early-Stage PD from control subjects, or iii) presence of at least one Early-Stage PD autoantibody biomarker in a subject is capable of forming at least a part of a basis of a diagnosis of the subject as having Early-Stage PD.

It has been discovered herein that neurodegenerative diseases, including Early-Stage PD, cause the production and release of cellular products as a result of cell damage related to ongoing pathology, some of which are both cell type- and organ-specific. These released cellular products (many of which are proteins), their break-down fragments and disease-related post-translational modifications enter the blood and lymph circulation, act as antigens, and elicit an immune response. This immune response leads to the production and appearance of a relatively large number of self-reactive autoantibodies in the blood.

Cells throughout the body share a vast number of proteins in common, but only a relatively small subset of autoantibodies are specifically reactive to the cells, tissues and organs involved in a particular disease. It has been discovered in accordance with the present invention that this response leads to a disease-specific autoantibody profile that is characteristic for each disease and the specific cell types involved. In addition, in individuals with concurrent diseases, it has been discovered herein that a specific pattern of autoantibodies reflects each of these concurrent, ongoing disease processes. Accordingly, the present invention relates to the specific pattern of PD biomarkers that are associated with Early-Stage PD as well as the target antigens of the autoantibody biomarkers.

Once inside the brain tissue, autoantibodies are free to bind selectively to any cells within the brain that possess and display the proper target antigens on their surfaces. If the autoantibody target is particularly abundant on a cell surface, the binding of many molecules of autoantibody can crosslink and immobilize this protein. If the target is an important receptor, the target and the cell can be rendered nonfunctional, leading to more global brain functional impairments. Thus, specific brain-reactive autoantibodies in human sera can put one at risk for specific diseases, such as Early-Stage PD. The invention described herein provides a method for the detection of these autoantibodies in human biological samples and their use as biomarkers for the detection and diagnosis of Early-Stage PD.

Thus in one embodiment, the present invention provides a method of identifying a subject who has or is at risk of developing Early-Stage PD comprising obtaining an immunoglobulin-containing biological sample from the subject, performing an assay to determine the presence or absence of one or more Early-Stage PD autoantibody biomarker in the biological sample, and identifying the subject as either with or at risk for developing Early-Stage PD if one or more of Early-Stage PD autoantibody biomarkers is present.

It was shown that blood-borne autoantibodies have potential to serve as useful biomarkers of disease (Han et al. *PloS one* 7, e32383 (2012) and Nagele et al. *PloS one* 6, e23112 (2011). These autoantibodies are abundant and ubiquitous in the blood, and are influenced by a variety of factors including age, gender, and the presence of ongoing disease (Nagele et al. *PloS one* 8, e60726 (2013), Avrameas *Immunology today* 12, 154-159 (1991), and Shoenfeld et al. *Journal of autoimmunity* 38, J71-73 (2012)). There is evidence that they function in the daily physiological clearance of cell and tissue debris from the blood; and it has been hypothesized that individual autoantibody profiles vary with the immune system's heightened response to the release of specific, pathology-associated debris (Nagele et al. *PloS one* 8, e60726 (2013), Jennette et al. *Kidney international* 78, 533-535 (2010), and Cohen *Trends in immunology* 34, 620-625 (2013)). In support of this, specific autoantibodies in human serum were previously identified to serve as biomarkers to diagnose mild-moderate stages of PD with an overall accuracy of 97.1%, with comparable results also obtained for mild-moderate Alzheimer's disease (AD), Han et al. *PloS one* 7, e32383 (2012) and Nagele et al. *PloS one* 6, e23112 (2011).

As disclosed herein, an autoantibody biomarker discovery strategy was used to identify autoantibody biomarker candidates useful for the detection and diagnosis of Early-Stage PD. Results confirmed that a small panel of autoantibody biomarkers detected in serum could differentiate Early-Stage PD patients from age-matched controls with an overall accuracy of 89.2%. It could also readily distinguish Early-Stage PD subjects from those with more clinically advanced, Mild-Moderate PD, as well as differentiate them from individuals afflicted with other neurodegenerative and non-neurodegenerative diseases like AD, multiple sclerosis, and breast cancer.

More specifically, sera were obtained from subjects enrolled in the DATATOP study through the Michael J. Fox Foundation and Parkinson's Study Group (DATATOP: a multicenter controlled clinical trial in early Parkinson's disease. Parkinson Study Group. *Archives of Neurology* 46, 1052-1060 (1989)). These subjects were diagnosed initially and later confirmed at follow-up with Early-Stage PD with 90% confidence. They participated in the DATATOP clinical trial aimed at testing the potential beneficial effects of two antioxidative therapies, deprenyl and tocopherol, on the progression of PD. These agents were found to have no discernable beneficial effects on PD progression. Autoantibody biomarker profiles for DATATOP subjects with Early-Stage PD were obtained and compared with age- and sex-matched controls as well as with sera from PD patients with more advanced (mild-moderate) disease.

As disclosed herein, a panel containing 50 autoantibody biomarkers was initially identified as being able to distinguish subjects with Early-Stage PD from age- and sex-matched controls. Their significance and predictive value were then verified using an independent Testing Set containing subject samples that were not involved in the biomarker discovery process. Results showed an overall accuracy for Early-Stage PD detection of 89.2%, a sensitivity of 94.2% and a specificity of 84.7%. ROC curve assessment of the utility of the diagnostic showed an AUC of 0.93 with 50 biomarkers and 0.92 with four biomarkers. Since it is generally considered desirable for a diagnostic test to have a sensitivity and specificity greater than 85% and a ROC curve AUC of 0.85, the two biomarker panels for Early-Stage PD detection described here exceed these criteria for the specific population studied (Henriksen et al. *Alzheimer's & dementia: the journal of the Alzheimer's Association* 10, 115-131 (2014). Among the 50 autoantibody biomarkers identified (Table 1), the top four represent the minimum number required for accurate detection and diagnosis of Early-Stage PD. Moreover, the same panel of four biomarkers is specific in differentiating Early-Stage PD from other neurological and non-neurological diseases, such as AD, MS, and breast cancer. Therefore, in at least some embodiments, methods of the present invention for detecting Early Stage PD follow the steps of identifying the presence of four (4) biomarkers.

Figure 3:
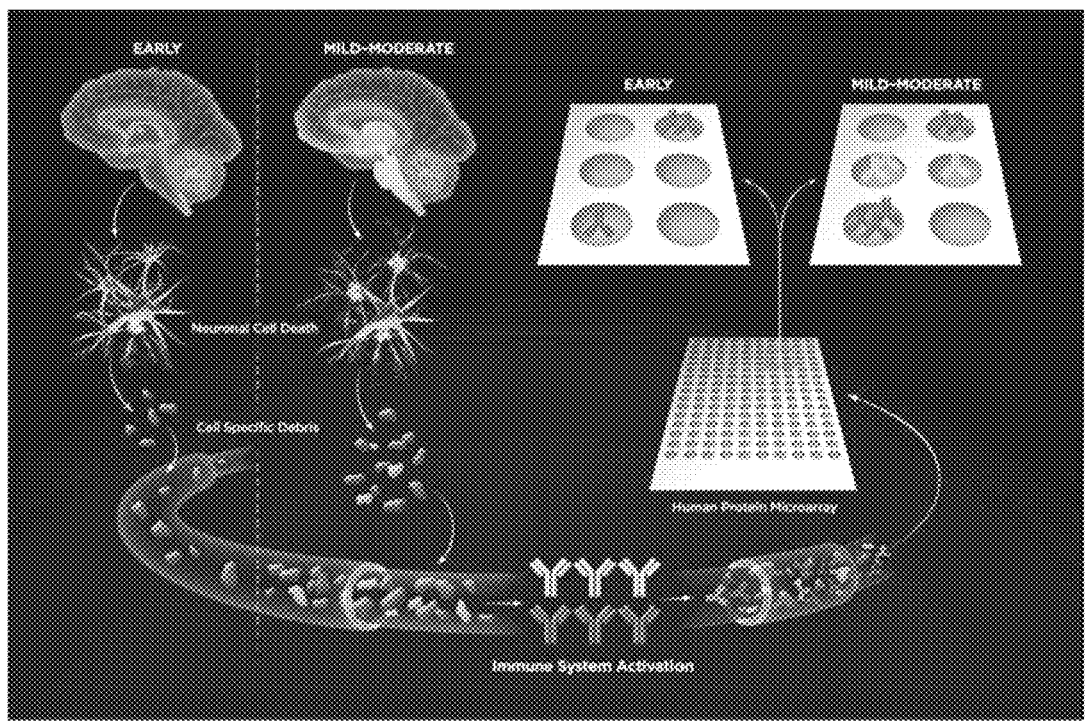
FIG. 3 is a diagram showing proposed origin of autoantibodies useful for PD diagnosis and staging. By the time symptoms emerge at Early-Stage PD, a substantial fraction of neurons in the substantia nigra (dot in brain) has already died. Cell debris (particles), subjected to variable degrees of degradation, are liberated into the surrounding brain tissue. Some debris makes its way into the blood, activates the immune system, and elicits the production of corresponding autoantibodies. In Early-Stage PD, the site of pathology and debris production is often highly localized, and the spectrum of disease-associated autoantibodies is likewise limited (dark autoantibodies). Escalation and spreading of PD pathology during later disease stages (e.g., mild-moderate PD) leads to more abundant and diverse debris and disease-associated autoantibody profiles. For each disease stage, autoantibodies exhibiting the most dramatic and consistent changes are selected as the useful biomarkers of the disease.

The two panels of 50 and four autoantibody biomarkers described here have also allowed one to distinguish Early-Stage PD from mild-moderate PD with an overall accuracy of 98.5%, a sensitivity of 94.2%, specificity of 84.7%, and a ROC curve AUC of 0.98 for the 50 biomarkers and 0.99 for the four biomarkers. A diagnostic test that can properly distinguish different stages of PD severity will make it possible to follow a patient's disease course, rate of progression, and response to therapies. This exciting capability is useful for physicians and their patients as well as for early enrollment of subjects into clinical trials and monitoring therapeutic efficacy through a patient's response to new drugs. Of course, for the latter, a positive patient response would be a delay in a patient's progression to the next disease stage or an improvement from the current disease state as evidenced by curtailed symptoms. Any slowing or stopping of disease progression resulting from diminished pathology would be expected to be accompanied by reduced debris production as well as a corresponding reduction in levels of disease-associated autoantibodies (FIG. 3).

It is widely recognized that the pathogenesis of a number of neurodegenerative diseases is initiated many years prior to the emergence of clinically useful symptoms. For effective and accurate identification of biomarkers directly linked to pathology, the selection of truly pathology-free controls is just as important as the selection of subjects with confirmed pathology. However, without the aid of telltale symptoms during prodromal phases of disease, it is difficult to ensure that age-matched controls being used for biomarker discovery are truly pathology-free. This may be especially problematic for diseases like AD where, due to a combination of high prevalence and a long prodromal period, a large fraction of individuals are likely to have pre-symptomatic pathology. This is much less of a problem with PD because of the relatively low prevalence of PD within the elderly population. Nevertheless, the difficulty of obtaining pathology-free controls would be expected to hinder biomarker discovery efforts as well as the possibility of achieving pre-symptomatic disease detection.

To investigate strategies that may aid in compensating for this inherent study limitation, the effects of purposely adding a subset of younger controls to the control subject pool were tested on diagnostic accuracy. It was predicted that adding truly pathology-free controls (albeit younger and non-age-matched) to the control subject group should improve diagnostic outcome by emphasizing the non-pathology features of autoantibody profiles common to both groups. For a disease with a relatively low prevalence, such as PD, it was speculated that the number of compensatory younger controls added should be relatively low—in this case perhaps no more than 5% of the total controls population. However, for diseases with a much higher prevalence and longer prodromal period, such as AD, the percentage of compensatory younger controls added should be higher.

As disclosed here, panels of autoantibody biomarkers can accurately differentiate Early-Stage PD subjects from age-matched controls using a minute volume of serum and human protein microarrays. Furthermore, they can distinguish Early-Stage PD subjects from those with more advanced disease as well as differentiate them from other neurodegenerative and non-neurodegenerative diseases with high accuracy. The development of a sensitive and specific, blood-based diagnostic test for Early-Stage PD could have a profound clinical impact on the early treatment of PD patients who currently rely on symptoms alone for diagnosis. The use of these autoantibody biomarkers would fundamentally change the way PD progression is monitored in trials of potential therapies. Accordingly, autoantibodies described herein can serve as dynamic and accurate diagnostic biomarkers of PD. Moreover, due to their proposed function in disease-specific debris clearance, the autoantibodies may serve as useful biomarkers for many diseases.

In another embodiment, the present invention provides a method for diagnosing Early-Stage PD in a subject in need of such diagnosis comprising obtaining an immunoglobulin-containing biological sample from the subject, performing an assay to determine the presence or absence of at least one autoantibody biomarker in the biological sample, and diagnosing Early-Stage PD if at least one Early-Stage PD autoantibody biomarker is present.

Another embodiment of this invention provides a method for detecting Early-Stage PD autoantibody biomarkers in a subject comprising obtaining an immunoglobulin-containing biological sample from the subject, and performing an assay to determine the presence or absence of one or more Early-Stage PD autoantibody biomarkers in the biological sample.

In a preferred embodiment of the invention, the immunoglobulin-containing biological sample is serum, plasma, whole blood, CSF, saliva, or sputum. A blood sample may be obtained by methods known in the art including venipuncture or a finger stick. CSF may be obtained by methods known in the art including a lumbar spinal tap. To obtain serum from blood, a sample of blood is received and centrifuged at a speed sufficient to pellet all cells and platelets, and the serum to be analyzed is drawn from the resulting supernatant. Sputum and saliva samples may be collected by methods known in the art. The biological samples may be diluted with a suitable buffer.

In a preferred embodiment of the invention, the assay used to determine the presence or absence of one or more Early-Stage PD autoantibody biomarkers in the biological sample is performed by contacting the biological sample with one or more target antigens that are specific for at least one Early-Stage PD autoantibody biomarker under conditions that allow an immunocomplex of the target antigen and the autoantibody biomarker to form, and detecting the presence of the immunocomplex.

Early-Stage PD autoantibody biomarkers may be identified by comparing the autoantibodies present in an immunoglobulin-containing sample from a subject having a neurodegenerative disease with autoantibodies present in an immunoglobulin-containing sample from an age-matched AD-free control subject. The target antigens for the autoantibody biomarkers present in the sample from the subject having Early-Stage PD but not present in the sample from the control subject provide the identification of Early-Stage PD autoantibody biomarkers. The sample is preferably serum or plasma.

In a preferred embodiment of the invention, the subject is a human.

Target Antigens

The term "target antigens" or just "antigens" as used herein includes protein and peptide antigens. In one embodiment, target antigens that have been identified as capable of being specifically bound by the Early-Stage PD autoantibody biomarkers are set forth in Table 1 below. Antigenic fragments of those target antigens disclosed in Table 1 are expressly considered covered by the present invention, so long as the autoantibody biomarkers of the present invention are capable of binding to the antigenic fragments thereof. Target antigens may comprise a protein antigen or antigenic fragments thereof, a polypeptide or peptide fragment thereof containing one or more epitopes recognized by the autoantibody biomarkers, or an epitope peptidomimetic that is recognized by the autoantibody biomarkers. The target antigens may be purified from natural sources, or produced recombinantly or synthetically by methods known in the art, and may be in the form of fusion proteins. The target antigens may be produced in vitro using cell-free translation systems. In one preferred embodiment, the target antigens are produced in a mammalian, insect or bacterial expression system to ensure correct folding and function. All of these methods may be automated for high throughput production.

The target antigens in Table 1 are identified by art-accepted names as well as database identification numbers. The database identification numbers refer to the publically available protein databases, for example, the National Center for Biotechnology Information (NCBI), which are well-known and accessible to those of ordinary skill in the art. One of ordinary skill in the art will realize that by being given a database identification number corresponding to a nucleotide sequence, one may also find the corresponding publicly available amino acid/polypeptide sequence of the target antigen from that source. Thus, one of ordinary skill in the art will realize that if provided a database identification number, such as, for example, a GenBank No. or Accession No. corresponding to a nucleotide sequence, such as, but not limited to a cDNA clone or mRNA sequence that codes for a target antigen of the present invention, that one may find the target antigens of the present invention from the GenBank No. or Accession No. corresponding to said nucleotide sequence. Or, alternatively, one may simply transcribe (if DNA including cDNA) and translate (RNA) to provide a polypeptide corresponding to the target antigens of the present invention.

Suitable methods for external production and purification of target antigens to be spotted on arrays disclosed herein include expression in bacteria, as disclosed for example by Venkataram et al. (2008) *Biochemistry* 47:6590-6601, in yeast, as disclosed for example by Li et al. (2007) *Appl Biochem Biotechnol.* 142:105-124, in insect cells, as disclosed for example by Altman et al. (1999) *Glycoconj J* 16:109-123, and in mammalian cells, as disclosed for example by Spampinato et al. (2007) *Curr Drug Targets* 8:137-146.

One having ordinary skill in the art will understand that modifications, including substitutions, including but not limited to conservative substitutions, additions, and deletions may be made to the amino acid/polypeptide sequences of the target antigens of the present invention, and that the substituted target antigens would still be covered by the present invention, so long as the autoantibody biomarkers may still bind to the target antigens or antigenic fragments thereof. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the target antigens the present invention can be replaced with other amino acid residues from the same side chain family and the altered target antigen can retain functional activity as described herein.

The term "homology" as used herein may refer to the existence of shared structure between two compositions. The term "homology" in the context of proteins may refer to the amount (e.g. expressed in a percentage) of overlap between two or more amino acid and/or peptide sequences. In the context of nucleic acids, the term may refer to the amount (e.g. expressed in a percentage) of overlap between two or more nucleic acid sequences. As used herein, the percent (%) homology between two sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm. Such homology is well-represented in the art via local alignment tools and/or algorithms, and may include pairwise alignment, multiple sequence alignment methods, structural alignment methods, and/or phylogenetic analysis methods. Specific examples include the following. The percent identity between two amino acid sequences can be determined using the algorithm of E. Meyers and W. Miller (Comput. Appl. Biosci, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) J. Mol. Biol. 215:403-10. BLAST protein searches can be performed with the XBLAST program, score=50, word-length=3 to obtain amino acid sequences homologous to the antibody molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used.

One having ordinary skill in the art will understand that post-translational modifications may be made to the amino acid/polypeptide sequences of the target antigens of the present invention, and such modified target antigens would still be covered by the present invention, so long as the autoantibody biomarkers may still bind to the target antigens or antigenic fragments thereof.

One of ordinary skill in the art will understand that the target antigens include, but are not limited to, gene products, synthetic polypeptides, recombinant polypeptides, fragments of polypeptides, and analogs, orthologs, paralogs, or homologs of gene products, synthetic polypeptides, so long as the autoantibody biomarkers may still bind to the target antigens or antigenic fragments thereof.

One having ordinary skill in the art will understand that the target antigens may be chemically modified, such as but not limited to, e.g. modifications made to individual amino acid residues, PEG-ylation, addition of sequence tags, reporter molecules, so long as the autoantibody biomarkers may still bind to the target antigens.

So long as the autoantibody biomarkers may still bind to the target antigens or antigenic fragments thereof, any modification made to the target antigens or antigenic fragments thereof is considered to be covered by this invention. The preferred antigenic fragments of the present invention are at least 85%, 90%, 95% or 98% homologous to the antigenic structures of the antigens of Table I and bind with disease related autoantibody biomarkers or have the same immunoreactivity characteristics as the target antigens of Table 1.

TABLE 1

Target Antigens

| Database ID | Protein Name | Proposed Function |
|---|---|---|
| NP_061120.3 | Serine/threonine-protein kinase MARK1 | Regulator of neuronal migration |
| NM_153339.1 | PUSL1 (tRNA pseudouridine synthase-like 1) | Regulator of tRNA processing |
| AF402002.1 | Interleukin-20 (IL20) | Proinflammatory and angiogenic cytokine |
| Q99731.1 | C-C motif chemokine 19 (CCL19) | Mediator of inflammatory and immunological responses |
| BC033758.1 | ADAP2 (Arf-GAP with dual PH domain-containing protein 2) | GTPase regulator |
| BC006105.1 | ATAT1 (Alpha-tubulin N-acetyltransferase 1) | Regulator of microtubule dynamics |
| NM_012241.2 | SIRT5 (NAD-dependent protein deacylase sirtuin-5, mitochondrial) | NAD-dependent lysine demalonylase and desuccinylase |
| BC059947.1 | CSAG1 (Putative chondrosarcoma-associated gene 1 protein) | Possible tumor antigen |
| XP_015296543.1 | Serine/threonine-protein kinase BRSK1 | Regulator of neuron migration and polarization |
| BC103660.1 | cDNA clone BC103660 | Unknown |
| Q96L34 | MAP/microtubule affinity-regulating kinase 4 | Implicated in nervous system development and cytoskeletal organization |
| BC002493.1 | TCF19 (Transcription factor 19) | Cell cycle regulator |
| NM_201403.1 | MOB3C (MOB kinase activator 3C) | Kinase regulator |
| NM_005030.2 | PLK1 (Serine/threonine-protein kinase PLK1) | Cell cycle regulator |
| BC051000.1 | TCL1B (T-cell leukemia/lymphoma protein 1B) | Protooncogene |
| NM_177524.1 | MEST (Mesoderm-specific transcript homolog protein) | Member of the alpha/beta hydrolyse superfamily |
| NM_152260.1 | RPUSD2 (RNA pseudouridylate synthase domain-containing protein 2) | Involved in pseudouridine synthesis |
| XM_373800.2 | PREDICTED: *Homo sapiens* hypothetical LOC388528 | Unknown |
| NM_080659.1 | C11orf52 (Uncharacterized protein C11orf52) | Unknown |
| BC036056.1 | FANCM (Fanconi anemia group M protein) | Involved in DNA repair |
| NM_024041.1 | *Macaca fascicularis* brain cDNA clone: QorA-12280 | Unknown |
| NM_018039.2 | KDM4D (Lysine-specific demethylase 4D) | Histone demethylase |
| NM_005205.2 | COX6A2 (Cytochrome c oxidase subunit 6A2, mitochondrial) | Member of the cytochrome C oxidase subunit 6A superfamily |
| NM_005469.2 | Acyl-coenzyme A thioesterase 8 | Acyl-CoA thioesterase |
| NM_180699.1 | SNRNP35 (U11/U12 small nuclear ribonucleoprotein 35 kDa protein) | Component of the U11/U12 snRNPs that are part of the U12-type spliceosome |
| NM_001697.1 | ATP5O (ATP synthase subunit O, mitochondrial) | Mitochondrial membrane ATP synthase |
| NM_001545.1 | ICT1 (Peptidyl-tRNA hydrolase ICT1, mitochondrial) | Peptidyl-tRNA hydrolase component of the mitochondrial large ribosomal subunit |
| NM_173578.1 | Human cDNA ORF Clone (C11orf72) | Unknown |
| XM_086879.4 | PREDICTED: *Homo sapiens* hypothetical LOC150371 | Unknown |
| NM_017692.1 | *Macaca fascicularis* brain cDNA clone: QorA-10370 | Unknown |

TABLE 1-continued

Target Antigens

| Database ID | Protein Name | Proposed Function |
|---|---|---|
| BC000190.1 | ZC3HC1 | Unknown |
| BC096708.1 | WT1-AS (Putative Wilms tumor upstream neighbor 1 gene protein) | Unknown |
| NM_022551.2 | RPS18 (40S ribosomal protein S18) | Component of 40S ribosomal subunit |
| XM_379114.1 | PREDICTED: Homo sapiens hypothetical protein LOC150577 (LOC150577) | Unknown |
| NM_016360.1 | TACO1 (Translational activator of cytochrome c oxidase 1) | Translational regulator |
| BC011924.1 | UNKL (Putative E3 ubiquitin-protein ligase UNKL) | Involved in ubiquitination of itself and other substrates |
| NM_003910.2 | BUD31 (Protein BUD31 homolog) | Transcriptional regulator |
| BC033230.1 | ZNF808 (Zinc finger protein 808) | Transcriptional regulator |
| XM_378879.2 | PREDICTED: Homo sapiens hypothetical LOC400763. (LOC400763) | Unknown |
| BC014452.1 | HCG1986256 | Unknown |
| XM_378350.2 | PREDICTED: Homo sapiens hypothetical LOC400027 | Unknown |
| NM_002147.2 | Homo sapiens homeobox B5 (HOXB5) | Transcription factor |
| BC009894.2 | PAPSS2 (Bifunctional 3'-phosphoadenosine 5'-phosphosulfate synthase 2) | Regulator of the sulfate activation pathway |
| NM_016101.3 | NIP7 (60S ribosome subunit biogenesis protein NIP7 homolog) | Involved in pre-rRNA processing and 60S ribosome subunit assembly |
| NM_002927.3 | RGS13 (Regulator of G-protein signaling 13) | GTPase regulator |
| NM_001008572.1 | Probable tubulin polyglutamylase TTLL1 | Catalytic subunit of the neuronal tubulin polyglutamylase complex |
| XM_085833.5 | PREDICTED: Homo sapiens hypothetical LOC147646 | Unknown |
| NM_014763.2 | MRPL19 (39S ribosomal protein L19, mitochondrial) | Structural component of mammalian mitochonridal ribosome |
| NM_003668.2 | MAPKAPK5 (MAP kinase-activated protein kinase 5) | Tumor suppressor involved in post-transcriptional regulation |
| NM_001002269.1 | EXOSC3 (Exosome complex component RRP40) | Involved in RNA processing and degradation |

Specific Target Antigens

Specific target antigens of the present invention that may be of interest include, but are expressly not limited to, the following target antigens. These antigens are meant to be exemplary to assist one of ordinary skill in the art and are explicitly non-exclusive embodiments of the invention. One of ordinary skill in the art will realize that in relation to the sequence data presented below, substitutions, modifications, additions, and deletions may be made while retaining the functional characteristic of the target antigens, namely that the autoantibody biomarkers of the present invention remain capable of binding to the target antigens. This expressly includes, but is not limited to, any of the antigenic fragments disclosed below, so long as the autoantibody biomarkers of the present invention are capable of binding to the antigenic fragments.

A. Serine/Threonine-Protein Kinase MARK1

Target antigen serine/threonine-protein kinase MARK1, also known as MAP/microtubule affinity-regulating kinase 1, is a serine/threonine kinase which is involved in cytoskeletal organization and biogenesis. Target antigen serine/threonine-protein kinase MARK1 is known to have the following antigenic fragments, all of which are considered to be covered by this present invention as potential target antigens. AA residues 59 to 311, "catalytic domain"; 331 to 371 "UBA domain"; 697 to 794"C-terminal, kinase associated domain 1, a phospholipid binding domain."

A nucleotide sequence coding for the target antigen MARK1 is reproduced below:

Accession No. NM_001286124.1

(SEQ ID NO: 1)

GCTGCTCCGCGCGCAGCCGGCTCGGGCCGCTCCTCCTGACTGAGGCGCGGCGGCGGCGGT

GGCTGTGACCGCGCGGACCGAGCCGAGACATTCGCGCCGGGGGATCGGGCGCCGCCGCTGGG

CCCCGGGCGCGTGGATGCGGCTGGGTCGGGCGGCGCCGTACACCTGAGGCGGAGAACGGGCGCG

GCGCGGGTGACGCTGTCAGGGCCGCGGTTCCTGACGCCCAGGCGCTCGCCAGGACGAGCCAGGCA

GTGATTTGAGGCACCGGCTTCACCTTCACCCATGGTCCGGAGAGCCTAGCGGGGCTCGCCACCGC

CTCCCGGCTCCCCTTCCACGCCTCATCCTGCCAGCCTCGCCGCCCCGCCAGCGCCGGGCAACCGC

CTCGCCCGAAGCCCTCCCTCGTTACTGTCCGCATACCCCGGCGGCGCCGCCGCGGGAAGCGGCTC

CCCCTCCTCTTCCTCCGCGTCCTCTTCCCTCTTTCCCCCGCCGGGGCCGCTTGTTGCACCGCCCC

-continued

```
GCGGCCTGCGGGAGCCGCTCGCCCCGGCCTTGTGCTCGCGTCCGCACCCCTTTCCTGTCGCCCCC

CGGGGCCCGCACCACAGCCCGGCCGGCGAGACCCCGGCCAGACCCCGCTGCCCGCACAAAATGTC

GGCCCGGACGCCATTGCCGACGGTGAACGAGCGGGACACGGAAAATCATACATCTGTGGATGGAT

ATACTGAACCACACATCCAGCCTACCAAGTCGAGTAGCAGACAGAACATCCCCCGGTGTAGAAAC

TCCATTACGTCAGCAACAGATGAACAGCCTCACATTGGAAATTACCGTTTACAAAAAACAATAGG

GAAGGGAAATTTTGCCAAAGTCAAATTGGCAAGACACGTTCTAACTGGTAGAGAGGTTGCTGTGA

AAATAATAGACAAAACTCAGCTAAATCCTACCAGTCTACAAAAGTTATTTCGAGAAGTACGAATA

ATGAAGATACTGAATCATCCTAATATAGTAAAATTGTTTGAAGTTATTGAAACAGAAGACTCT

CTATTTAGTCATGGAATACGCGAGTGGGGGTGAAGTATTTGATTACTTAGTTGCCCATGGAAGAA

TGAAAGAGAAAGAGGCCCGTGCAAAATTTAGGCAGATTGTATCTGCTGTACAGTATTGTCATCAA

AAGTACATTGTTCACCGTGATCTTAAGGCTGAAAACCTTCTCCTTGATGGTGATATGAATATTAA

AATTGCTGACTTTGGTTTTAGTAATGAATTTACAGTTGGGAACAAATTGGACACATTTTGTGGAA

GCCCACCCTATGCTGCTCCCGAGCTTTTCCAAGGAAAGAAGTATGATGGGCCTGAAGTGGATGTG

TGGAGTCTGGGCGTCATTCTCTATACATTAGTCAGTGGCTCCTTGCCTTTCGATGGCCAGAATTT

AAAGGAACTGCGAGAGCGAGTTTTACGAGGGAAGTACCGTATTCCCTTCTATATGTCCACAGACT

GTGAAAATCTTCTGAAGAAATTATTAGTCCTGAATCCAATAAAGAGAGGCAGCTTGGAACAAATA

ATGAAAGATCGATGGATGAATGTTGGTCATGAAGAGGAAGAACTAAAGCCATATACTGAGCCTGA

TCCGGATTTCAATGACACAAAAAGAATAGACATTATGGTCACCATGGGCTTTGCACGAGATGAAA

TAAATGATGCCTTAATAAATCAGAAGTATGATGAAGTTATGGCTACTTATATTCTTCTAGGTAGA

AAACCACCTGAATTTGAAGGTGGTGAATCGTTATCCAGTGGAAACTTGTGTCAGAGGTCCCGGCC

CAGTAGTGACTTAAACAACAGCACTCTTCAGTCCCCTGCTCACCTGAAGGTCCAGAGAAGTATCT

CAGCAAATCAGAAGCAGCGGCGTTTCAGTGATCATGCTGGTCCATCCATTCCTCCTGCTGTATCA

TATACCAAAAGACCTCAGGCTAACAGTGTGGAAAGTGAACAGAAAGAGGAGTGGGACAAAGATGT

GGCTCGAAAACTTGGCAGCACAACAGTTGGATCAAAAAGCGAGATGACTGCAAGCCCTCTTGTAG

GGCCAGAGAGGAAAAAATCTTCAACTATTCCAAGTAACAATGTGTATTCTGGAGGTAGCATGGCA

AGAAGGAATACATATGTCTGTGAAAGGACCACAGATCGATACGTAGCATTGCAGAATGGAAAAGA

CAGCAGCCTTACGGAGATGTCTGTGAGTAGCATATCTTCTGCAGGCTCTTCTGTGGCCTCTGCTG

TCCCCTCAGCACGACCCCGCCACCAGAAGTCCATGTCCACTTCTGGTCATCCTATTAAAGTCACA

CTGCCAACCATTAAAGACGGCTCTGAAGCTTACCGGCCTGGTACAACCCAGAGAGTGCCTGCTGC

TTCCCCATCTGCTCACAGTATTAGTACTGCGACTCCAGACCGGACCCGTTTTCCCCGAGGGAGCT

CAAGCCGAAGCACTTTCCATGGTGAACAGCTCCGGGAGCGACGCAGCGTTGCTTATAATGGGCCA

CCTGCTTCACCATCCCATGAAACGGGTGCATTTGCACATGCCAGAAGGGGAACGTCAACTGGTAT

AATAAGCAAAATCACATCCAAATTTGTTCGCAGGGATCCAAGTGAAGGCGAAGCCAGTGGCAGAA

CCGACACCTCAAGAAGTACATCAGGGGAACCAAAAGAAAGAGACAAGGAAGAGGGTAAAGATTCT

AAGCCGCGTTCTTTGCGGTTCACATGGAGTATGAAGACCACTAGTTCAATGGACCCTAATGACAT

GATGAGAGAAATCCGAAAAGTGTTAGATGCAAATAACTGTGATTATGAGCAAAAAGAGAGATTTT

TGCTTTTCTGTGTCCATGGAGACGCTAGACAGGATAGCCTCGTGCAGTGGGAGATGGAAGTCTGC

AAGTTGCCACGACTGTCACTTAATGGGGTTCGCTTCAAGCGAATATCTGGGACATCTATTGCCTT

TAAGAACATTGCATCAAAAATAGCAAATGAGCTTAAGCTGTAAAGAAGTCCAAATTTACAGGTTC

AGGGAAGATACATACATATATGAGGTACAGTTTTTGAATGTACTGGTAATGCCTAATGTGGTCTG

CCTGTGAATCTCCCCATGTAGAATTTGCCCTTAATGCAATAAGGTTATACATAGTTATGAACTGT
```

-continued

```
AAAATTAAAGTCAGTATGAACTATAATAAATATCTGTAGCTTAAAAAGTAGGTTCACATGTACAG

GTAAGTATATTGTGTATTTCTGTTCATTTTCTGTTCATAGAGTTGTATAATAAAACATGATTGCT

TAAAAACTTGTATAGTTGTCTAGATTTCTGCACCTGAATGTATGTTTGATGCTTTGATTTGAAAA

TGTTCTTCCCTGTTATTTACATTCTGGTGGGTTTTTAAAATTCTTACCTCCATCATGCAATTTTG

AAAATTGTGTCCAGAATTAAAAGTGCATAGAAATAGCCTTTACAATTGTAGCATGGACCTTTAAA

AATTGTTTTAAAATCTTATTTAAATTTAAACCAGAAGCTGAAAAATAGATCAGCTTTATTATACA

CAAAATTATTACTGCTTATCTTTGCTCTTTTCCTTGTTATCCCGCAAGGTTTAGTTGAGAAGATA

CAAAATGTTTACAGTGTTGGCACTTAGAGTTTTTAAATTCAAGTACATGAAATTCAGTAATAGCA

TTGCCTTGAGCTAACTAGGAAGTACCGGGAAAAAAGTTAAATCTACATCAAGTTTCTTTTGAACT

TTGAAGTGTTTTCTGACCCACTGCTAACTGTAGCAACAAAATTTAAAAGAAAAAAAACATACTTT

ATCTGGCTATTATAACATAAACTGTCACGTAGGTTTGCTGCCTTCAGAATACCGCAATTTAATTG

CGGGAATATAATAATATTGGGACTGTTTCACAGCACAAACTCATCTTTACAGTGTTGATCAATGC

ATCAGTTAAGAAATAATGCCACCTCAGGAATTAACTGGCATTGGGAACATTTGCCTCATTCTCCT

GCTATCCTCTTCATTCACCCCTGCCACTGTAATATCTATAAGTACTTAAGAGACTTGTGAGCAAA

ACATACTATTTATAACAGTATATGATTGATTTATGCTTATGTGGTTGTTCAGTTTGTTCCCATGT

AACTCGTTTGTTTTAAATATTTTGCCAGATTTCTTGTATTTATTCCACATCATTATGCCTATAAT

GTGCCGCTTTGTGATTGGGCATTTGCCTACTTTTCTTTCATAATTAGTGATATATGCGATGTAAA

ACCACTAGTAAAGGTACATTTAATACTTGTTATTTTATACTGAATTAGCCTTGGAGGTTGACTG

TGCAATGTTATTTACTGTTGTAATTACTGTAATACCAACATATGGGCCCCATCTGCACACTCCTG

AAAAACAGAAAGTGTATTCAAATTTTATCAGTTTAAAGAAAATAAAGCTGTGATAAATACTGTAA

TTCCAACCTACATTAGAAGGTCTAAGTGTAGGTGATGTGCCATTCCATAATGGCTTCCAGACTAG

GGTGAATTTTATGTTCTGTACTGTACTGTGATGTAGCTTTCTTCTGTAACAGTTATGTTTTAAAA

TTAAGTGAGTTTTTTTTTGCCTTAGCAAAGGGTGGTGTTTGAAAAAAAAAATGTGTAGCCCCTT

TTTAACCTAGTGTTCATTCAAAAAAAAAATTGATGCAAATCTTTATTCACTTTCACTGGTGCACAC

TGAAATTTTACTTGAACAGTTCTCATAATAAAGCACTTGTCTTTTGCTCTTTATCAGAATGTGAA

TTACCTGTTTTCTGGTACAAAAGTATTCTGTATGAGGAGTTTATTGTATGTGTTCTAAATTTAGT

TGGCAAAGGGTGAAGCTGTGAAGGTTTTCAAGATTATTGAAACTATGAAGGTTTCTTGTCATTAT

GACAAGAAAGTTTAATCTTTTTATAGGAATTCCTGTCACTGAAATACGTTTTTAAAAAAATAGAC

TCATGTGTTTTCCACGGTAGAAACTGATATTTTTTACATTTTCTCACTGTGGCCAACTCTTCTG

TGTTTGTAGAAAGGAATTTGACTTCAATATCTTTTATGAACTAAAAATGAAATCTTGATACTCAC

TTTAGATTTTTCATTTTATGTGTTCATGACAACATAAATATTTTTCAAAGATTTAGAGGAATTTT

GCAATGTGTTTGCATAAATAAATACCAGTTTATGTTCACCGGCTATGTGATACCAGGATTTCCTT

GGCTTCTGTTGAAATATTTGATATGACATCCCTTATATTAAATTAATTATTTTGTAAAAAAA

AAAAAAAAAA,
```

An amino acid sequence for target antigen MARK1 is reproduced below:

Accession No. NP_061120.3

(SEQ ID NO: 2)

```
MSARTPLPTVNERDTENHTSVDGYTEPHIQPTKSSSRQNIPRCRNSITSA

TDEQPHIGNYRLQKTIGKGNFAKVKLARHVLTGREVAVKIIDKTQLNPTS

LQKLFREVRIMKILNHPNIVKLFEVIETEKTLYLVMEYASGGEVFDYLVA

HGRMKEKEARAKFRQIVSAVQYCHQKYIVHRDLKAENLLLDGDMNIKIAD

FGFSNEFTVGNKLDTFCGSPPYAAPELFQGKKYDGPEVDVWSLGVILYTL

VSGSLPFDGQNLKELRERVLRGKYRIPFYMSTDCENLLKKLLVLNPIKRG

SLEQIMKDRWMNVGHEEEELKPYTEPDPDFNDTKRIDIMVTMGFARDEIN
```

DALINQKYDEVMATYILLGRKPPEFEGGESLSSGNLCQRSRPSSDLNNST

LQSPAHLKVQRSISANQKQRRFSDHAGPSIPPAVSYTKRPQANSVESEQK

EEWDKDVARKLGSTTVGSKSEMTASPLVGPERKKSSTIPSNNVYSGGSMA

RRNTYVCERTTDRYVALQNGKDSSLTEMSVSSISSAGSSVASAVPSARPR

HQKSMSTSGHPIKVTLPTIKDGSEAYRPGTTQRVPAASPSAHSISTATPD

RTRFPRGSSSRSTFHGEQLRERRSVAYNGPPASPSHETGAFAHARRGTST

GIISKITSKFVRRDPSEGEASGRTDTSRSTSGEPKERDKEEGKDSKPRSL

RFTWSMKTTSSMDPNDMMREIRKVLDANNCDYEQKERFLLFCVHGDARQD

SLVQWEMEVCKLPRLSLNGVRFKRISGTSIAFKNIASKIANELKL,

B. tRNA Pseudouridine Synthase-Like 1 (PUSL1)

A nucleotide sequence coding for target antigen PUSL1 is reproduced below:

```
Accession No. NM_153339.1
                                      (SEQ ID NO: 3)
CGCCTCTGACGCCACCGGCTGGGCTCCGCCATGAGTTCGGCGCCGGCCTC

AGGCTCCGTGCGCGCGCGCTATCTTGTGTACTTCCAGTACGTGGGCACCG

ACTTTAACGGGGTCGCGGCCGTCAGGGGCACTCAGCGCGCCGTCGGGGTC

CAGAACTACCTGGAGGAGGCCGCCGAGCGGCTGAATTCCGTGGAGCCGGT

CAGGTTCACCATCTCCAGCCGCACGGACGCCGGGGTCCACGCCCTGAGCA

ACGCGGCGCACCTGGACGTCCAGCGCCGCTCAGGCCGGCCGCCCTTCCCG

CCCGAGGTCCTGGCCGAGGCCCTCAACACACACCTGCGGCACCCGGCCAT

CAGGGTCCTGCGGGCCTTCCGAGTGCCCAGCGACTTCCACGCTCGTCACG

CAGCCACGTCCCGGACCTACCTGTACCGCCTGGCCACTGGCTGTCACCGG

CGTGATGAGCTGCCGGTGTTTGAACGCAACCTATGCTGGACTCTCCCGGC

AGACTGCCTGGATATGGTCGCCATGCAGGAAGCCGCCCAGCACCTCCTCG

GCACACACGACTTCAGCGCCTTCCAGTCCGCTGGCAGCCCGGTGCCGAGC

CCCGTGCGAACGCTGCGCCGGGTCTCCGTTTCCCCAGGCCAAGCCAGCCC

CTTGGTCACCCCCGAGGAGAGCAGGAAGCTGCGGTTCTGGAACCTGGAGT
```

```
TTGAGAGCCAGTCTTTCCTGTATAGACAGGTACGGAGGATGACGGCTGTG

CTGGTGGCCGTGGGGCTGGGGGCTTTGGCACCTGCCCAGGTGAAGACGAT

TCTGGAGAGCCAAGATCCCCTGGGCAAGCACCAGACACGTGTAGCCCCAG

CCCACGGCTTATTCCTCAAGTCAGTGCTGTACGGGAACCTCGGTGCTGCC

TCCTGCACCCTGCAGGGGCCACAGTTCGGGAGCCACGGATGACCCTGGAC

ACTCAAGCCAAAGTTAGGCCACACCAGGCCCAACCCTGTGCTGGTCAAGC

CAGGGCAGTCACAGCTGCTTGGGGCCCACAGCACTGCTGCCTGGTCTCCA

CAGTAGCCTCCCTGCCCGGGTCCCAGCACCCTGGATGCCCGTCTCTGTCC

CAGGCGGGATGGGGCACAGTGCAGGACACAGCCATGTACACCAAGAAGAG

AGTACCAAGTAGTCTTTTGTTCAGCTTTTACTGGAAACTGCTGTCTAGGA

CCACCTGCCCTAACCAGGAATAAAGGCAAGACAGCCTGGAAAAAAAAAAA

AAAAAAAAAAA,
```

An amino acid sequence for target antigen PUSL1 is reproduced below:

```
Accession No. NP_699170.1
                                      (SEQ ID NO: 4)
MSSAPASGSVRARYLVYFQYVGDFNGVAAVRGTQRAVGVQNYLEEAAERL

NSVEPVRFTISSRTDAGVHALSNAAHLDVQRRSGRPPFPPEVLAEALNTH

LRHPAIRVLRAFRVPSDFHARHAATSRTYLYRLATGCHRRDELPVFERNL

CWILPADCLDMVAMQEAAQHLLGTHDFSAFQSAGSPVPSPVRTLRRVSVS

PGQASPLVTPEESRKLRFWNLEFESQSFLYRQVRRMTAVLVAVGLGALAP

AQVKTILESQDPLGKHQTRVAPAHGLFLKSVLYGNLGAASCTLQGPQFGS

HG,
```

C. Interleukin-20 (IL20)

Target antigen Interleukin-20, also known IL-20, is a cytokine structurally related to interleukin 10 (IL-10). IL-20 has been shown to transduce its signal through signal transducer and activator of transcription.

A nucleotide sequence coding for target antigen IL-20 is reproduced below:

```
Accession No. AF402002.1
                                      (SEQ ID NO: 5)
TAAATAATGGGAAGCCTTTCAACTTGAAACAGGCTCCTAGGAGACCAGAAGCAGCAGCCT

TTCCTGAGCTCAGGTAAGAGATCTTACCCTCTACTGACACTGCTCACGTTGTTGTGAGGATCACC

TACTTCTCCTAATCATTTACCCAGGTATGTTCAAGGTCACATCTAAAGGACCCTTTTCCACGAGG

ACAAAATCTCTTTGAGGACAAATAATCATCATGTTTATCTTTGTACTTCAGTACCTAGCACAACA

TTCAAGACAGCGGGTGCTCATTAAATGCTCATCAAATTGTTAGTTCAGGACAACTAACATCAATC

TCTACTTAAAATGAATTGATCACTTGCTCTGTGCTAAGTGTATAAATCATAGATTATTGTATTTA

AATAATCGATTTAAAATCAAAACAATTTCTGGGTTAAGTTTAATTATCACCATTTTGGGGTTAAG

AAAATTAAACTCAGAGGTGAGTTGACTTGTCCAAGGTCACATAGAGGTAGGGTGGCCAACTCATT

CCAGTTTACCTGTGGTTTTTCCAGTTTTAAAACTGAAATTTTCGTATTTCAGGAACCATTCCCTG

CCCCCCAACCTCAGTCCTGGGTAAACTGGAATGACCCACATCAATGGAAACTAGTAAAGCGAGGA

TTTATTTGGACCCAGTTCTCTTGTCTCCAAACCCAGAGTCCTCTTTGATTCTTTTGGGTTTGGTT
```

-continued

```
TGCTTTTTTCCTTTTCCTACATTTGACAGTATCTCGAGTGGTCACAAATGTAAAAAATGTCTAGC
ATATTGCCTGGCATATAGGAAAAATTCAGTAAGTGATAATGATTATCAGTGCTGTGCCAAGCTAT
GGAGCCAGCCATATATATATGGATGTGTGCATATATATATATGATGTGTGTGTATATATATATGT
CTTTATAAATTTTATGTATTTATTTCTTTCAAAAATATTAAAGTATTTGAGAAAATTGAAAAATT
AAAAAGTAGGTTTATTACGACTCATGACTTTAAGTTTAAATATTTTATTTCTGCCCCAAACAAAA
TTTATTATAATTTTACTGTCCTGGTTTTAAGGGAAGGAAACTCATCAATAATATTTTCATCATAT
GCTTTTGAGAAACAAAGTTAACCATTAAGAATGAAACATGAAAACATGTGAATAGTGGTACAAAT
TTTTCCTTTTGCTTCAATATGGCTCAGCATGGCACTGTCGAATTTTGTCTTTATATAAAATTTTG
ATATTTTGTTTGTCATAAGCTTTTTAATTCATTTTTATATTGCACTAAAATATTTTTATCTTGAT
GACTGAGGTTTTTAGTGCTCCCTTAAATTTTGCACCTAAAATGAGTGCCTCAATTGTTTTACCC
TAACCTCAGCCCATTATTATTTTATCTTAAAACTCAGCAAACACCCTAACCTGCTCTCTTACTGA
GGAGGCTCGCCCAAGAATAAATGAGTTCCGTCATTGCCTTTCTTCTCTGACTTTTGGGACCATTT
GCTTGGTCTAGGACCTGAGTTGCAGGTCCAGGAAAGCGTGTACTCTCGAATCCACCCAGGAGTGC
CTGACTACAGTCCTCCTGCAGAGGGCGCTGTGGAGTCCCAGACACGAGTGTTAGGTGGAATCGGG
CTGATTGCCCATCACGTCTTGCCTTTCCCTGGCAGTAGGCTTGTTATGAAATCATTGACTTTCTA
TTTGCCTCTGGGGCTTAAGCGAATCTGTTACCCTCAAATAACCTATCTGATCTCAGACAAATGCC
AAACAGAGCTCAGTTTCTCTGCCCTGTGGGTGGCCATAAAATCCAGACAATTTCCCCCTAGGTGT
TTTCGATGGCGCAGCCACAGCTTCTGTGAGATTCGATTTCTCCCCAGTTCCCTGTGGGTCTGAG
GGGACCAGAAGGGTGAGCTACGTTGGCTTTCTGGAAGGGGAGGCTATATGCGTCAATTCCCCAAA
ACAAGTTTTGACATTTCCCCTGAAATGTCATTCTCTATCTATTCACTGCAAGTGCCTGCTGTTCC
AGGCCTTACCTGCTGGGCACTAACGGCGGAGCCAGGATGGGGACAGAATAAAGGAGCCACGACCT
GTGCCACCAACTCGCACTCAGACTCTGAACTCAGACCTGAAATCTTCTCTTCACGGGAGGCTTGG
CAGTTTTTCTTAGTAAGTTGCGTGGATGGGCCACACTGTCTGAGGCCAGATAAGGCTGTTCTCTT
CCCCTGACCCCCCACCCCTCACCCCGTGGACACTTGGAGGAGGGGAAACTCAGTAAGTCATGCTC
TCTTCTTTGAATTCCTAGCTCCTGTGGTCTCCAGATTTCAGGCCTAAGATGAAAGCCTCTAGTCT
TGCCTTCAGCCTTCTCTCTGCTGCGTTTTATCTCCTATGGACTCCTTCCACTGGACTGAAGACAC
TCAATTTGGGAAGCTGTGTGATCGCCACAAACCTTCAGGAAATACGAATGGATTTTCTGAGATA
CGGGGCAGTGTGGTACGTAAGCGGGTATCTACCTCTCCTGAAAGCCTTTTCTCTTCCTTCCTTGT
CCGTTTCTCTTTCCTGGCAGTACTGGCAGTGTAATCATAAAAAGAGGCAGGCTGGGGATTCCTTA
CCCGGGGGATGTATTCCAAAGAAATAACTGTAGTTCAAATATTTAAAATGTTTTGGGAAAGGACA
CCTCCCACTAGTTCTTGGCAGGGAGTGGATGAGAAGTCTTGATATTGAAGACCCTGGCAGCAGGC
ACTGACTCATCCTTGCTTGTTTTGTCTTCTTCTGTTTAGCAAGCCAAAGATGGAAACATTGACAT
CAGAATCTTAAGGAGGACTGAGTCTTTGCAAGACACAAAGGTATGTGCTTGGCCCAGACAAACTC
TGGGAGGAGGAGTGGAGTGGGAGCATCTCCATCACCCTGGTCTTGTCTCTGCTCTCCCCTTTCCC
CTCACCAATATACCTGTGGTTTTTTGCAGCCTGCGAATCGATGCTGCCTCCTGCGCCATTTGCTA
AGACTCTATCTGGACAGGGTATTTAAAAACTACCAGACCCCTGACCATTATACTCTCCGGAAGAT
CAGCAGCCTCGCCAATTCCTTTCTTACCATCAAGAAGGACCTCCGGCTCTGTGTGAGTGTGGGTC
TTGGGTGACAGGATGCATCTCAGCACACAGCTTCAATGGCTTAGCAACTAAACTCTCTTTCCTAC
CTCCATTTAATGGATGGAGAAACTGAGTCCAAAAGTTCTAATAATCTGTGTTGAGACATGTGACT
AGGTAATAAGAACTCAGTTTTATTGACTTTTCGGTATATGCTCTAGGCAAAAAGTACTTTGCAAA
```

-continued

```
GTCTAAAGAACTATAAGATGCTAACTATTTGATATTAATGATAACTCTGTTGTCTTTGAAATTAT
ACTTTTTCTGTAGGTGAGGTATCCTACAGTATATTAGTGCGTCCTCTGTCTAGGCAGTCAATTAG
TAGACCATTGAGCTTGACCTCAGAATATAGTCTGAATAGGACCTAGGAATTCAATTCTTTTTTTT
TTTTTTCTCAATGGGGGCTCAAAGAGCTCTGGGATAGAGCTCCTAGACTACAGCTGGGGGTTGTG
GGGAGGCCAGATGGGGTACGGGGATGGCAAATGCCTTCAGTACTGCCTGCCTATTTCTAAAAAG
AAGTGATGAGTTCCATGTTTGAGCCTAAAAGGTGGCTTCCTCTCCTAGCTGATGATGAACTTAAT
GATTCCAAATGTGAGGTCTGAAAGAGCTTTTCTATAGGAATAAGCATCCTCAGGGTTGTGGGTGA
AAGAGTAGAGTTTCTACCTGCTTCATGTCAATGGCAAAAAATCAGAATCTGTAATATAATCTATT
ATTCTTTGGGTCCTTTTCAGCATGCCCACATGACATGCCATTGTGGGGAGGAAGCAATGAAGAAA
TACAGCCAGATTCTGAGTCACTTTGAAAAGGTATATGCGACTTTGGCATTGATTGGGATGGGTGT
GTTTTAAGAACTGAGATCATAGGTAGGTGGGATGGTTATTCACTGTTAGACATCCTGTAGCCTTC
AGGTTCATAGCCCTCTGAAATCATGAGGACCAGCCCTTGCTTTAACCCAGGGGACACCCATCCAG
GCTCTAGAGGAGTACCCTCTCTGGGTGATGCTCTGGAAATGGAAAGGGAATGGCCATGATTCCAT
CAAGTCACTACAGTGACATCTGGATCTTTTAGCTGCACAAACCAGAGGCAATAGTTTTACAATGT
TCACACACTTCTATGTACCTTTGAAAACACTCACAATTTCACACACACACCCATGCCATTCAATT
TCTCACCTTCACACCTTCTCATGTCTGCCAGGAAGGCCTGGATTTCACTCCTCACTGACTAAATC
CTACTCATCCTTTAAAGACTCAGCCTGGGCATCACTTTCAGGAAGGTGCTGGCTCCTTCTCTCAG
AGTTAGATGCCTCCCACATCATCTTGTAGGAATTTCATCCCTTTATTCACCACACTACATTTTAG
TTGCCTGTTTTTGCCAGTCTCCTCACTCAACTGTGGATAGGGATTGTGCCATTCACCTTTTCATC
CCTAACCATCAGCTAGGTGATTGGCACAATCAATATCTGTTCAACTGATGTGTGCACCGTAGGCA
ACCCCTACACACACACAGGCACGTGCACACACACACACACACGTTTCTTAAAGAAAATAGC
TTGATTATTTTGATCTCTGTGATTCAAGAGTCTTAAGTAGCAGTTTTACTTCTGCTACCCCCTTG
CACCTCAGTTTCTGTACATAAGACCAGGGTGATGAACTCAATGATTTCCCTTCCTTGTGTGATAT
CTTGAGATTCTATAACTTCTTTAAGTGCTTCATCTTGAAAAGAATGCTCTGCTTACAATTGTCAG
CAGACCTATCCATAAAAGAGATAGGTCCTGGAGCAAATGCTGTCTCATGAATTGCTAACCACATG
GGTGTGTGTCTCTTTCAGCTGGAACCTCAGGCAGCAGTTGTGAAGGCTTTGGGGGAACTAGACAT
TCTTCTGCAATGGATGGAGGAGACAGAATAGGAGGAAAGTGATGCTGCTGCTAAGAATATTCGAG
GTCAAGAGCTCCAGTCTTCAATACCTGCAGAGGAGGCATGACCCCAAACCACCATCTCTTTACTG
TACTAGTCTTGTGCTGGTCACAGTGTATCTTATTTATGCATTACTTGCTTCCTTGCATGATTGTC
TTTATGCATCCCCAATCTTAATTGAGACCATACTTGTATAAGATTTTGTAATATCTTTCTGCTA
TTGGATATATTTATTAGTTAATATATTTATTTATTTTTTGCTATTTAATGTATTTATTTTTTAC
TTGGACATGAAACTTTAAAAAAATTCACAGATTATATTTATAACCTGACTAGAGCAGGTGATGTA
TTTTTATACAGTAAAAAAAAAAAACCTTGTAAATTCTAGAAGAGTGGCTAGGGGGGTTATTCATT
TGTATTCAACTAAGGACATATTTACTCATGCTGATGCTCTGTGAGATATTTGAAATTGAACCAAT
GACTACTTAGGATGGGTTGTGGAATAAGTTTTGATGTGGAATTGCACATCTACCTTACAATTACT
GACCATCCCCAGTAGACTCCCCAGTCCCATAATTGTGTATCTTCCAGCCAGGAATCCTACACGGC
CAGCATGTATTTCTACAAATAAAGTTTTCTTTGCATAACATCTGCTTGGAGTTTGCAAATGTTTC
AAGAGCAGAGACCATGTTGAGGATAAGTTTGAATCTCATTTCACCCCAGGTCCTCTTGCTCCTTT
GAGGAAGAAGATGTAGGAACCTCGATCTTCTCTCCTGCAGATTTCATCCTCAGCTCTATCTCC
TAATTCATACTGCTCTGACCCCACGACTGCCCTCCTCTCAAAAGGACTGTGACAGAGTGAGGGGC
TTCAGCCATCTCTGCTTTCGCCTCATTGGCTTGGAGCACTGCCCTTTCTATACCTCTGTTTTCTT
```

-continued

```
TCTCACCCCATACCCTTGCAAGACAAATTACAATGGGCATGAGGCGCTATTATAAAGGTTAAAAA

CACACAGGTGCAAAGTGTAGGTCTAGAGTCTTGCCCAGACAGGTGTATGAGCCCCCTTTTGAGGC

CCTTCCATTTTGGATTCTGTCCAGCCTCAGAGTTTAGGTTGTTACCAGATCAAGTCCTTATCTTT

GTGTCCAACTATTAAGTCAGTGTTTTCTTTCCAGGCCCCCTTCAGGTTGAGTGTCCCTGGACACT

GAGGAGCCAGAGTTCTGGCCTGGGCTGGTTCCTTCCTTCTTCCCCCACCTCACTCTGAAGCGCAC

CCCCAATTTAGTTGCTTAGTTTTCTCAGTCTCAGAAACAACAGTCTCAGGCTGATTCCCTGGGTC

CTAAAGATAACTCTCCTTACTGCTTTAATTTCTACTCCCTGTTCTTAGCCTGGGCCCTGATATAG

TTTCAATGACTTTAACTTTTGATAACTCTCATTATACAAGTAACAGCTGCCCAACAGAAAAGAAA

TTTTGGAAGAAAACAGAAATATAAAGAAGAAAATTAAAATCACCCATAATCTCACCACCCTCAGA

CAACCACTTTTAAACATTTATGCTTATTTTTTCCAGATATTTTTTGATGGGTTCAAATCATGACT

CAGCTCTCA,
```

An amino acid sequence for target antigen IL-20 is reproduced below:

```
Accession No. AAK84423.1
                                          (SEQ ID NO: 6)
MKASSLAFSLLSAAFYLLWTPSTGLKTLNLGSCVIATNLQEIRNGFSEIR

GSVQAKDGNIDIRILRRTESLQDTKPANRCCLLRHLLRLYLDRVFKNYQT

PDHYTLRKISSLANSFLTIKKDLRLCHAHMTCHCGEEAMKKYSQILSHFE

KLEPQAAVVKALGELDILLQWMEETE,
```

D. C—C motif chemokine 19 (CCL19)

Target antigen C—C motif chemokine 19 (CCL19), also known as "MIP-3-beta Recombinant Human Protein," is a bioactive chemokine. Target antigen C—C motif chemokine 19 is known to have the following antigenic fragments, all of which are considered to be covered by this present invention as potential target antigens. AA residues 1 to 21, "signal peptide"; 22 to 98; "mature chain"; 26 to 29 "beta-strand region"; 27 to 87 "chemokine_CC_DCCL, subgroup based on the presence of a DCCL motif involving two N-terminal cysteine residues"; 42 to 49 "beta-strand region"; 51 to 53 "hydrogen bonded turn"; 59 to 64 "beta-strand region"; 69 to 72 "beta-strand region"; 74 to 76 "beta-strand region"; 77 to 90 "helical region."

An amino acid sequence for C—C motif chemokine 19 is reproduced below:

```
Accession No. Q99731.1
                                          (SEQ ID NO: 7)
MALLLALSLLVLWTSPAPTLSGTNDAEDCCLSVTQKPIPGYIVRNFHYLL

IKDGCRVPAVVFTTLRGRQLCAPPDQPWVERIIQRLQRTSAKMKRRSS,
```

Detection and Diagnostic Methods

In one embodiment, the present invention provides a method for detecting Early-Stage PD autoantibody biomarkers in a subject in need of such detection comprising obtaining an immunoglobulin-containing biological sample from the subject, and performing an assay to determine the presence or absence of one or more of the biomarkers in the biological sample.

In another embodiment, the present invention provides a method for diagnosing Early-Stage PD in a subject in need of such diagnosis comprising obtaining an immunoglobulin-containing biological sample from the subject, performing an assay to determine the presence or absence of one or more Early-Stage PD autoantibody biomarkers in the biological sample, and diagnosing Early-Stage PD if one or more PD diagnostic biomarkers are present.

In a preferred embodiment, the subject is a human subject. In a preferred embodiment of the invention, the immunoglobulin-containing biological sample is serum, plasma, whole blood, CSF, saliva, or sputum. A blood sample may be obtained by methods known in the art including venipuncture or a finger stick. CSF may be obtained by methods known in the art including a lumbar spinal tap. Serum and plasma samples may be obtained by centrifugation methods known in the art. Sputum and saliva samples may be collected by methods known in the art. The biological samples may be diluted with a suitable buffer before conducting the assay. In a preferred embodiment, the biological sample is serum, plasma, or whole blood.

Assays to determine the presence or absence of one or more Early-Stage PD autoantibody biomarkers in the biological sample are performed by contacting the sample with one or more antigens that are specific for an Early-Stage PD autoantibody biomarker under conditions that allow an immunocomplex of the antigen and the antibody to form, and detecting the presence of the immunocomplex.

An antigen may comprise a protein antigen listed in Table 1 above, or a polypeptide or peptide fragment thereof containing one or more epitopes recognized by the Early-Stage PD autoantibody biomarker, or an epitope peptidomimetic that is recognized by the Early-Stage PD autoantibody biomarker. Peptidomimetics include, for example, D-peptides, peptoids, and β-peptides. The antigens may be purified from natural sources, or produced recombinantly or synthetically by methods known in the art, and may be in the form of fusion proteins. The antigens may be produced in vitro using cell-free translation systems. In one preferred embodiment, the antigens are produced in a mammalian or insect expression system to ensure correct folding and function. All of these methods may be automated for high throughput production.

Assays and conditions for the detection of immunocomplexes are known to those of skill in the art. Such assays include, for example, competition assays, direct reaction assays and sandwich-type assays. The assays may be quantitative or qualitative. In one preferred embodiment, the assay utilizes a solid phase or substrate to which the antigens are directly or indirectly attached, such as a microtiter or microassay plate, slide, magnetic bead, non-magnetic bead, column, matrix, membrane, or sheet, and may be composed of a synthetic material such as polystyrene, polyvinyl chloride, polyamide, or other synthetic polymers, natural polymers such as cellulose, derivatized natural polymers such as cellulose acetate or nitrocellulose, and glass, for example glass fibers. The substrate preferably comprises a plurality of individually addressable antigens immobilized on the surface. The individually addressable antigens are preferably immobilized on the surface to form an array. The substrates may be used in suitable shapes, such as films, sheets, or plates, or may be coated onto or bonded or laminated to appropriate inert carriers, such as paper, glass, plastic films, or fabrics. In a preferred embodiment, the substrate is a slide or a bead.

Methods for attaching the antigens to the support or substrate are known in the art and include covalent and non-covalent interactions. For example, diffusion of applied proteins into a porous surface such a hydrogel allows non-covalent binding of unmodified protein within hydrogel structures. Covalent coupling methods provide a stable linkage and may be applied to a range of proteins. Biological capture methods utilizing a tag (e.g., hexahistidine/Ni-NTA or biotin/avidin) on the protein and a partner reagent immobilized on the surface of the substrate provide a stable linkage and bind the protein specifically and in reproducible orientation.

In one preferred embodiment, the antigens are coated or spotted onto the support or substrate such as chemically derivatized glass, or a glass plate coated with a protein binding agent such as, but not limited to, nitrocellulose.

In one preferred embodiment the antigens are provided in the form of an array, and preferably a microarray. Protein microarrays are known in the art and reviewed for example by Hall et al. (2007) *Mech Ageing Dev* 128:161-167 and Stoevesandt et al. (2009) *Expert Rev Proteomics* 6:145-157, the disclosures of which are incorporated herein by reference. Microarrays may be prepared by immobilizing purified antigens on a substrate such as a treated microscope slide using a contact spotter or a non-contact microarrayer. Microarrays may also be produced through in situ cell-free synthesis directly from corresponding DNA arrays.

Suitable methods for external production and purification of antigens to be spotted on arrays include expression in bacteria, as disclosed for example by Venkataram et al. (2008) *Biochemistry* 47:6590-6601, in yeast, as disclosed for example by Li et al. (2007) *Appl Biochem Biotechnol.* 142:105-124, in insect cells, as disclosed for example by Altman et al. (1999) *Glycoconj J* 16:109-123, and in mammalian cells, as disclosed for example by Spampinato et al. (2007) *Curr Drug Targets* 8:137-146.

Suitable methods for in situ ("on-chip") protein production are disclosed, for example, by Ramachandran et al. (2006) *Methods Mol. Biol* 2328:1-14 and He et al. (2008) *Curr. Opin Biotechnol* 19:4-9.

Other methods by which proteins are simultaneously expressed and immobilized in parallel on an array surface are also known in the art and may be used in accordance with the present invention. For example, in the Protein In Situ Arrays (PISA) method (He et al. (2001) *Nucleic Acids Res* 29: e73), proteins are made directly from DNA, either in solution or immobilized, and become attached to the array surface as they are made through recognition of a tag sequence. The proteins are expressed in parallel in vitro utilizing a cell free system, commonly rabbit reticulocyte or *E. coli* S30, to perform coupled transcription and translation. In this method, protein expression is performed on a surface which is precoated with an immobilizing agent capable of binding to the tag. Thus after each protein is translated, it becomes fixed simultaneously and specifically to the adjacent surface, while the other materials can subsequently be washed away. Microarrays are produced directly onto glass slides, either by mixing the DNA with the cell free lysate system before spotting or by a multiple spotting technique (MIST) in which DNA is spotted first followed by the expression system.

In the system known as Nucleic Acid Programmable Protein Array (NAPPA) (Ramachandran et al. (2004) *Science* 305:86-90), transcription and translation from an immobilized (as opposed to a solution) DNA template allow conversion of DNA arrays to protein arrays. In this method, biotinylated cDNA plasmids encoding the proteins as GST fusions are printed onto an avidin-coated slide, together with an anti-GST antibody acting as the capture entity. The cDNA array is then covered with rabbit reticulocyte lysate to express the proteins, which become trapped by the antibody adjacent to each DNA spot, the proteins thereby becoming immobilized with the same layout as the cDNA. This technology generates a protein array in which the immobilized proteins are present together with DNA and a capture agent.

Another suitable method for generating a protein array is the DNA Array to Protein Array (DAPA) method. This method for in situ protein arraying uses an immobilized DNA array as the template to generate pure protein arrays on a separate surface from the DNA, and also can produce multiple copies of a protein array from the same DNA template (He et al. (2008) *Nature Methods*, 5:175-7). Cell-free protein synthesis is performed in a membrane held between two surfaces (e.g., glass slides), one of which is arrayed with DNA molecules while the other surface carries a specific reagent to capture the translated proteins. Individual, tagged proteins are synthesized in parallel from the arrayed DNA, diffuse across the gap and are subsequently immobilized through interaction with the tag-capturing reagent on the opposite surface to form a protein array. Discrete spots which accurately reflect the DNA in position and quantity are produced. Replicate copies of the protein array can be obtained by reuse of the DNA.

Array fabrication methods include robotic contact printing, ink-jetting, piezoelectric spotting and photolithography. For example, purified antigens of the invention that are produced and purified externally may be spotted onto a microarray substrate using a flexible protein microarray inkjet printing system (e.g., ArrayJet, Roslin, Scotland, UK) to provide high quality protein microarray production. The precise rows and columns of antigens may be converted to detectable spots denoting both the presence and amount of diagnostic biomarkers that have been bound.

The production of the microarrays is preferably performed with commercially available printing buffers designed to maintain the three-dimensional shape of the antigens. In one preferred embodiment, the substrate for the microarray is a nitrocellulose-coated glass slide.

The assays are performed by methods known in the art in which the one or more antigens are contacted with the biological sample under conditions that allow the formation of an immunocomplex of an antigen and an antibody, and detecting the immunocomplex. The presence and amount of the immunocomplex may be detected by methods known in the art, including label-based and label-free detection. For example, label-based detection methods include addition of a secondary antibody that is coupled to an indicator reagent comprising a signal generating compound. The secondary antibody may be an anti-human IgG antibody. Indicator reagents include chromogenic agents, catalysts such as enzyme conjugates, fluorescent compounds such as fluorescein and rhodamine, chemiluminescent compounds such as dioxetanes, acridiniums, phenanthridiniums, ruthenium, and luminol, radioactive elements, direct visual labels, as well as cofactors, inhibitors and magnetic particles. Examples of enzyme conjugates include alkaline phosphatase, horseradish peroxidase and beta-galactosidase. Methods of label-free detection include surface plasmon resonance, carbon nanotubes and nanowires, and interferometry. Label-based and label-free detection methods are known in the art and disclosed, for example, by Hall et al. (2007) and by Ray et al. (2010) Proteomics 10:731-748. Detection may be accomplished by scanning methods known in the art and appropriate for the label used, and associated analytical software.

In one preferred embodiment of the present invention, fluorescence labeling and detection methods are used to detect the immunocomplexes. Commercially available slide scanners (e.g. the Genepix 4000B slide scanner (Molecular Devices, Inc.) with associated analytical software may be used. In one preferred embodiment, the immunocomplex is probed with fluorescent-labeled (e.g., Alexa-Fluor (Invitrogen)) anti-human antibody and the intensity of fluorescence at each protein spot is measured using a microarray scanner. Commercially available software (e.g. GenePix Pro 5.0 software (Axon instruments)) may be used to extract the net median pixel intensities for individual features from the digital images produced by the scanner. Data may be normalized by comparing median values of multiple identical control spots in different regions of the same array.

Detection of diagnostic immunocomplexes is indicative of the presence of Early-Stage PD autoantibody biomarkers in the biological sample, and thus a positive diagnosis of Early-Stage PD.

The results of the method described above can provide an Early-Stage PD diagnostic biomarker profile for the patient that is useful to diagnose Early-Stage PD and optimize a treatment regimen for PD. The method also can be used for identifying a subject who has or is suffering from developing PD without knowledge, wherein the subject can be identified if one or more of the Early-Stage PD autoantibody biomarkers is present.

In at least another embodiment, a diagnostic system for detecting an Early-Stage PD autoantibody biomarker in a subject who has or is at risk for developing Parkinson's Disease by (a) obtaining an immunoglobulin-containing biological sample from the subject, (b) conducting an immunoassay to detect at least four target antigens or antigenic fragments thereof specific for Early-Stage PD, (c) detecting the presence or absence of an immunocomplex, wherein the presence of an immunocomplex is indicative of the presence of the Early-Stage PD autoantibody biomarker in said patient and absence of such immunocomplex is indicative of absence of Early-Stage PD (d) generating a report identifying said patients who have Early Stage PD or are at risk of developing Early Stage PD and (e) optimizing the treatment plan in patients in need thereof by administering proper anti-Parkinson's treatment regimen.

Substrates and Microarrays

In yet another embodiment, the present invention provides a substrate on which one or more antigens that are specific for an Early-Stage PD autoantibody biomarker are immobilized. The present invention also provides, in another embodiment, a microarray comprising a substrate on which one or more antigens that are specifically bound by an Early-Stage PD autoantibody biomarker are immobilized.

The substrates and microarrays may be made as described hereinabove and are useful for creating Early-Stage PD diagnostic biomarker profiles and for the diagnosis of Early-Stage PD. An antigen may comprise a protein antigen listed in Table 1, or a polypeptide or peptide fragment thereof containing one or more epitopes recognized by the Early-Stage PD autoantibody biomarker, or an epitope peptidomimetic that is recognized by the PD diagnostic biomarker. Peptidomimetics include, for example, D-peptides, peptoids, and β-peptides. The substrate and microarrays may contain, as the antigen, at least one of the protein antigens listed in Table 1 or fragments thereof containing one or more epitopes recognized by the Early-Stage PD autoantibody biomarker.

In another embodiment, the substrate and microarrays may contain, as the antigen, at least one of the protein antigens listed in Table 1 or a polypeptide or peptide fragment thereof containing one or more epitopes recognized by the Early-Stage PD diagnostic biomarker, or an epitope peptidomimetic that is recognized by the Early-Stage PD diagnostic biomarker. Peptidomimetics include, for example, D-peptides, peptoids, and β-peptides. In another preferred embodiment of the present invention, the substrate and microarrays contain at least two, or at least three, or at least four, or at least five, or at least six, or at least seven, or at least eight, or at least nine, or all of the protein antigens listed in Table 1 or polypeptides or peptide fragments thereof containing one or more epitopes recognized by the Early-Stage PD autoantibody biomarker, or epitope peptidomimetics that are recognized by the Early-Stage PD autoantibody biomarkers listed in Table 1.

Microarray may be prepared on a glass surfaces with a variety of coatings including but not limited to nitrocellulose, FAST™, FullMoon™, SuperEpoxy™, SuperAldehyde™, SuperNHS™, Ni-NTA, PATH, Nextirion, Nexterion H thin film, epoxysilane or aldehydesilane or other similar coatings. Those of ordinary skill in the art can appreciate the equivalent coatings that can be employed as the suitable substrate. In some embodiments, the substrate can be a nitrocellulose-coated glass slide.

Besides the protein antigen in Table 1, or a polypeptide or peptide fragment thereof, many other protein antigens and polypeptides or peptide fragments thereof can be included in substrates or microarrays of this invention. Examples of these other protein antigens include those disclosed in US20140364328, WO2014018903, WO2013023144, WO2013010003, and WO2011142900, the contents of which are incorporated by reference in their entireties. These documents disclose additional markers for PD and markers for other disorders such as other neurodegenerative diseases and certain cancers. These substrates and microarrays are useful for profiling subjects or patents suspected of having one or more of these conditions and disorders.

In another embodiment, the methods of using the presently disclosed microarray requires detection of at least 4 complex formations between at least 4 autoantigens and at least 4 autoantibodies, wherein formation of such complex formations indicates the existence of Early Stage Parkinson's disease. In another embodiment, methods of establishing the correlation between the autoantibodies and Early Stage Parkinson's are described. In yet another embodiment, methods of identifying and screening candidate therapeutic regimens and anti-Parkinson's therapeutic agents are described that would reduce the associated biomarkers, degree of complex formation between the instant biomarkers and their respective antigens. In another embodiment, such candidate agents are capable of reducing the disease associated biomarkers, inhibiting or reducing the formation of autoantibody and their target autoantigens.

Diagnostic Kits

In a further embodiment, the present invention provides a kit for detecting Early-Stage PD-specific antibodies in a sample. A kit comprises one or more antigens that are specific for an Early-Stage PD autoantibody biomarker and means for determining binding of the antigen to the biomarker in the sample. The kit may also comprise packaging material comprising a label that indicates that the one or more antigens of the kit can be used for the identification of PD. Other components such as buffers, controls, detection reagents, and the like known to those of ordinary skill in art may be included in such the kits. The kits are useful for detecting Early-Stage PD autoantibody biomarkers and for diagnosing PD.

A kit may contain, in an amount sufficient for at least one assay, any combination of the components described herein, and may further include instructions recorded in a tangible form for use of the components. In some applications, one or more reaction components may be provided in pre-measured single use amounts in individual, typically disposable, tubes or equivalent containers. With such an arrangement, the sample to be tested for the presence of a target can be added to individual tubes or substrates and assay carried out directly. The amount of a component supplied in the kit can be any appropriate amount, and may depend on the target market to which the product is directed. General guidelines for determining appropriate amounts may be found in, for example, Joseph Sambrook and David W. Russell, Molecular Cloning: A Laboratory Manual, 3rd edition, Cold Spring Harbor Laboratory Press, 2001; and Frederick M. Ausubel, Current Protocols in Molecular Biology, John Wiley & Sons, 2003.

The kits of the invention can comprise any number of additional reagents or substances that are useful for practicing a method of the invention. Such substances include, but are not limited to: anticoagulants (e.g., EDTA and heparin), reagents (including buffers) for lysis of cells, divalent cation chelating agents or other agents that inhibit unwanted proteases, control antibodies for use in ensuring that the components of reactions are functioning properly, and wash solutions. The kits of the invention can be provided at any temperature. For example, for storage of kits containing protein components or complexes thereof in a liquid, it is preferred that they are provided and maintained below 0° C., preferably at or below −20° C., or otherwise in a frozen state.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

The term "about" generally refers to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The term "biological sample" refers to a sample obtained from an organism (e.g., patient) or from components (e.g., cells) of an organism. The sample may be of any biological tissue, cell(s) or fluid. The sample may be a "clinical sample" which is a sample derived from a subject, such as a human patient. Such samples include, but are not limited to, saliva, sputum, blood, blood cells (e.g., white cells), amniotic fluid, plasma, semen, bone marrow, and tissue or fine needle biopsy samples, urine, peritoneal fluid, and pleural fluid, or cells therefrom. Biological samples may also include sections of tissues such as frozen sections taken for histological purposes. A biological sample may also be referred to as a "patient sample." A biological sample may also include a substantially purified or isolated protein, membrane preparation, or cell culture.

As used herein, the term "contacting" and its variants, when used in reference to any set of components, includes any process whereby the components to be contacted are mixed into same mixture (for example, are added into the same compartment or solution), and does not necessarily require actual physical contact between the recited components. The recited components can be contacted in any order or any combination (or subcombination), and can include situations where one or some of the recited components are subsequently removed from the mixture, optionally prior to addition of other recited components. For example, "contacting A with B and C" includes any and all of the following situations: (i) A is mixed with C, then B is added to the mixture; (ii) A and B are mixed into a mixture; B is removed from the mixture, and then C is added to the mixture; and (iii) A is added to a mixture of B and C. "Contacting a template with a reaction mixture" includes any or all of the following situations: (i) the template is contacted with a first component of the reaction mixture to create a mixture; then other components of the reaction mixture are added in any order or combination to the mixture; and (ii) the reaction mixture is fully formed prior to mixture with the template.

Treatment Methods

Until now, prior art treatment methodologies of PD rely primarily on conclusions derived from extensive subjective assessments which, in turn, are dependent on the presentation of characteristic symptoms. However, these presentations are often apparent only after the disease is well underway and the brain has already sustained considerable damage to vital brain cells. In at least one aspect of the present invention, early diagnosis of PD based on the immune system's response to an early stage of the disease means provides a conclusive diagnosis long before symptoms emerge and too much brain damage has occurred.

In at least one embodiment, treatments including prophylactic measures are described in patients with a plasma profile indicative of early stage PD. In another embodiment, methods of treatment of early stage PD are described comprising diagnosing patients suffering from early stage PD and treating said patients in accordance to proper treatment regimen. In at least one embodiment, such treatments are administered before the disease has progressed past the point of therapeutic efficacy. In diseases with exceptionally long prodromal periods, early diagnosis would allow patients to avail themselves of treatments much sooner than was previously possible, altering the traditional course of the disease in their favor.

Proper treatment regimens may include but are not limited to dietary modifications to reduce neuronal oxidative stress, daily physical exercise, drug treatment including identification of suitable subjects for enrollment into clinical trials. In at least one embodiment, patients diagnosed or detected with early stage PD may start low dose anti-Parkinson's agents, including antioxidants such as tocopherol.

In at least one embodiment, the anti-Parkinson's agents may include levodopa preparations, and for others, an initial prescription may be given for one of the agonists, an MAO inhibitor or an anticholinergic. The choice of drug treatment depends on many variables including symptom presentation, other concurrent health issues (and the medications being used to treat them) and a person's age, and symptomatology, prevalence of existing biomarkers and frequency of factors such as patient's metabolism, and life style. In at least one embodiment, the specific medication regimen includes low dose Carbidopa/levodopa combination therapy, dopamine agonists, anticholinergics, MAO-inhibitors, COMT inhibitors or other known treatment methods in the art. Low dose treatments may include dosing ranges that is from 10 to 99%, or 15-95%, 30-90%, or 45-75% of the normal and/or regulatory agency approved doses for treatment of Parkinson's.

Accordingly, in some embodiments of the present invention, upon being diagnosed as having Early-Stage PD, a patient is administered one or more anti-Parkinsonian agent. "Anti-Parkinsonian agent" as used herein is defined as any therapeutic compound or composition that is used to prevent, treat, or mitigate Parkinson's Disease or any symptoms associated with Parkinson's Disease, and is specifically intended to cover at least the following examples.

The most widely utilized therapy for treatment PD involves administering therapeutically effective amounts of levodopa (L-dopa) in one or more formulations or compositions, such as levocarb (carbidopa/levodopa). Methods for preparing L-dopa and L-dopa prodrugs are known in the art, as well as their use and formulation may be found at, for example, U.S. Pat. Nos. 3,686,409, 3,878,043, 4,962,223, 4,983,400, 5,607,969 7,671,089, 8,735,382, and US Patent Publication Nos. US/2007/0027216 and US/2008/0255235, incorporated by reference herein in their entirety. Levocarb may be administered, for example, through a continuous infusion. Continuous infusion may be preferable, for example, in those patients who have fluctuation in their response to levocarb. Blood levels of carbidopa and levodopa remain constant in continuous infusion cases. Side effects of L-dopa and levocarb include dyskinesia (LID), and tolerance to L-dopa may build up over time. Administration of levocarb is generally between 0.01 mg and 1 g daily, generally between 50 mg to 500 mg, with a general starting dosage such as 100 mg L-dopa/25 mg carbidopa 3× daily, although administration may be changed over time according to patient's physiological characteristics.

Other therapeutic methods and treatments include dopamine agonists, including but not limited to pramipexole, ropinirole, and rotigotine. Dopamine agonists may be either long-acting or short-acting, for example Apo morphine. Dopamine agonists do not become metabolized into dopamine such as L-dopa, and as such may not be generally as effective. However, such agonists may last longer than L-dopa and may be used in combination with L-dopa, particularly where L-dopa is not administered in a continuous infusion. Side-effects for dopamine agonists are similar to L-dopa, but may also include hallucinations and other compulsive behaviors. Dosages for dopamine agonists are generally increased over time, and may be administered in a variety of ways, such as tablets, capsules, or by injection, continuous infusion, or by patches.

MAO-B inhibitors are another class of compounds suitable for treatment of Parkinson's. These may include, for example, selegiline and rasagiline. MAO-B inhibitors prevent the breakdown of dopamine by mimicking monoamine oxidase B (MAO-B). MAO-B inhibitors may be administered alongside L-dopa and/or levocarb, but carry similar risks of side-effects as with dopamine agonists. MAO-B inhibitors carry additional risks beyond those of dopamine agonists, and are not used in combination with anti-depressants or other narcotics due to potentially life-threatening reactions. MAO-B inhibitors may be administered via standard oral routes, such as in disintegrating tablets, and may be administered via other routes known in the art. MAO-B inhibitor dosage may be between 0.01 and 10 mg dosages, with ordinary dosages being between 0.5 mg and 1 mg doses given once or twice per day.

Other treatment methods include COMT inhibitors. Entacapone is the primary medication for this class, although tolcapone is an available therapeutic compound, which is not widely utilized due to risk of liver failure. COMT inhibitors block the enzyme catechol-O-methyltransferase (COMT), which is an enzyme that breaks down dopamine. COMT inhibitors, like L-dopa and levocarb, may result in dyskinesia (LID). Entacapone is generally administered between 50 and 2,000 mg/day, with dosage being one 200 mg tablet administered (optionally) with L-dopa/levocarb from once a day up to about 8 times a day.

Further potential pharmaceutical-based treatment methods include anticholinergics, and amantadine, but these are not used as often today because of the advance of preferable medications, such as those described herein. However, amantadine may still be prescribed in order to provide short-term relief of symptoms, particularly in Early-Stage PD, even though amantadine is generally recognized to be less effective than L-dopa at later stages. Thus, administration of Amantadine may be a first choice therapy after a positive diagnosis by the compositions, methods and kits of the present invention. Amantadine may be administered according to a number of routines known in the art.

Antibody-based therapies are another potential possibility, and while no FDA approved biologics for treatment of Parkinson's exist as of the time of this invention, potential candidates exist, including but not limited to LRRK2 (leucine-rich repeat kinase 2) antibodies. Additional antibodies include alpha-synuclein antibodies. Alpha-synuclein was the first gene to be linked with PD, and is a major component of Lewy bodies and is believed to be a promising link for PD pathogenesis. DJ-1 antibodies remain another area of interest, and are thought to act as a sensor for oxidative stress in the cell. These antibodies described herein may be human antibodies, humanized antibodies, murine antibodies, chimeric antibodies, rat antibodies, and other antibody constructs and may be administered according to methods known in the art.

Non-pharmaceutical or biologic based therapies include experimental treatments such as deep brain stimulation (DBS). An electrode is inserted through an opening in the skull and implanted within a specific brain area to which electrical impulses are provided. This may provide relief to the patient suffering from PD.

EXAMPLES

Example 1

This example describes material and methods used in Examples 2-7 below.

Approval for the use of serum samples in this study was obtained from the University of Medicine and Dentistry of New Jersey—School of Osteopathic Medicine and the Rowan-Stratford Institutional Review Boards.

Human Samples

103 Early-Stage PD samples were obtained from the Michael J. Fox Foundation (New York, N.Y.) in coordination with the Parkinson Study Group (Boston, Mass.). These samples came from subjects participating in the DATATOP study, which was a clinical trial investigating the potential beneficial effects of two anti-oxidative therapies, deprenyl and tocopherol, to delay the time at which patients progress to disability requiring levodopa treatment (DATATOP: a multicenter controlled clinical trial in early Parkinson's disease. Parkinson Study Group. *Archives of Neurology* 46, 1052-1060 (1989)). Diagnosis of PD was made with follow-up with 90% confidence by the DATATOP clinical investigators, and each patient was determined to have a Hoehn and Yahr scale score ranging from 1 to no greater than 2. Twenty-nine mild-moderate PD and 50 mild-moderate Alzheimer's disease serum samples were obtained from Analytical Biological Systems, Inc. (Wilmington, Del.). Thirty stages 0-2 breast cancer (BC) serum samples were obtained from Asterand, Inc. (Detroit, Mich.), and 30 multiple sclerosis (MS) patient serum samples were obtained from BioServe Biotechnologies Ltd (Beltsville, Md.). Healthy age- and sex-matched control serum samples were obtained from several sources: 40 from Analytical Biological Systems, Inc.; 65 from BioServe Biotechnologies Ltd.; 28 from Asterand Inc.; and 23 from The New Jersey Institute for Successful Aging at Rowan University (Stratford, N.J.). All samples were handled using standard procedures and stored at −80° C. until use. Demographic characteristics of the study population are displayed in Table 4.

Human Protein Microarrays

To identify autoantibodies in human sera, Invitrogen's ProtoArray v 5.0 Human Protein Microarrays (Cat. No. PAH0525020, Invitrogen, Carlsbad, Calif., USA), each containing 9,486 unique human protein antigens (www.invitrogen.com/protoarray), was used. All proteins were expressed as GST fusion proteins in insect cells, purified under native conditions, and spotted in duplicate onto nitrocellulose-coated glass slides. Arrays were probed with serum and scanned according to the manufacturer's instructions. Briefly, microarrays were blocked using Blocking Buffer (Cat. No. PA055, Invitrogen) and each was incubated with serum diluted to 1:500 in washing buffer. After washing, arrays were probed with anti-human IgG (H+L) conjugated to AlexaFluor 647 (Cat. No. A-21445, Invitrogen) diluted 1:2,000 in washing buffer. Arrays were then washed, dried, and immediately scanned with a GenePix 4000B Fluorescence Scanner (*Molecular Devices*, Sunnyvale, Calif., USA).

Microarray Data Analysis

Fluorescence data was acquired by aligning the Genepix Array List (GAL) onto the microarray using the Genepix Pro analysis software. The resulting Genepix Results (GPR) files were imported into Invitrogen's Prospector 5.2 for analysis. The "group characterization" and "two-group comparison" features in the IRBP Toolbox within Prospector then enabled M-statistical analysis of differential autoantibody expression between the two groups. Autoantibodies were sorted into descending order by difference of prevalence between early stage PD and control groups, and the top 50 most differentially expressed autoantibodies were chosen as potential diagnostic biomarkers. All data is MIAME compliant and raw data has been deposited in a MIAME compliant database (GEO).

The predictive classification accuracy of the selected biomarkers in the Training Set, Testing Set, and then in both sets combined was tested with Random Forest (RF), another significance algorithm run as an R package (v 4.6-10), using the default settings. Selected biomarkers were tested with the RF model and classification accuracy is reported in a confusion matrix and misclassifications as an Out-Of-Bag (OOB) error score. Receiver operating characteristic curves (ROCs) were generated using R (3.02) packages ROCR (v 1.0-5) and pROC (v 1.7.3).

Example 2 Selection of a Panel of Autoantibody Biomarkers for Early-Stage PD Diagnosis Previously published data from inventors' laboratory has highlighted the potential utility of autoantibodies as blood-based biomarkers for diagnosing mild-moderate PD (Han et al. *PloS one* 7, e32383 (2012)). Here, the same strategy was used to search for biomarkers useful for Early-Stage PD detection (FIG. 1). To achieve this, 103 Early-Stage PD serum samples from patients with a clinical diagnosis of PD at 90% confidence and 111 age- and sex-matched control samples (total n=214) were randomly separated into a Training Set and Testing Set (Table 4). The Training Set contained 52 Early-Stage PD samples and 56 controls, while the Testing Set contained 51 Early-Stage PD samples and 55 controls. Human protein microarrays containing 9,486 antigens were probed with Training or Testing Set sera. Using Prospector analysis software, 2,470 autoantibodies with a significantly (p<0.05) higher prevalence in the Early-Stage PD group compared to controls were identified in the Training Set as potential diagnostic biomarkers. From this list, the top 50 most differentially expressed autoantibodies in the Early-Stage PD group were chosen as a working diagnostic panel of biomarkers (Table 1).

Example 3 Verification of Biomarkers Via Training and Testing Set Analysis

Figure 2A:
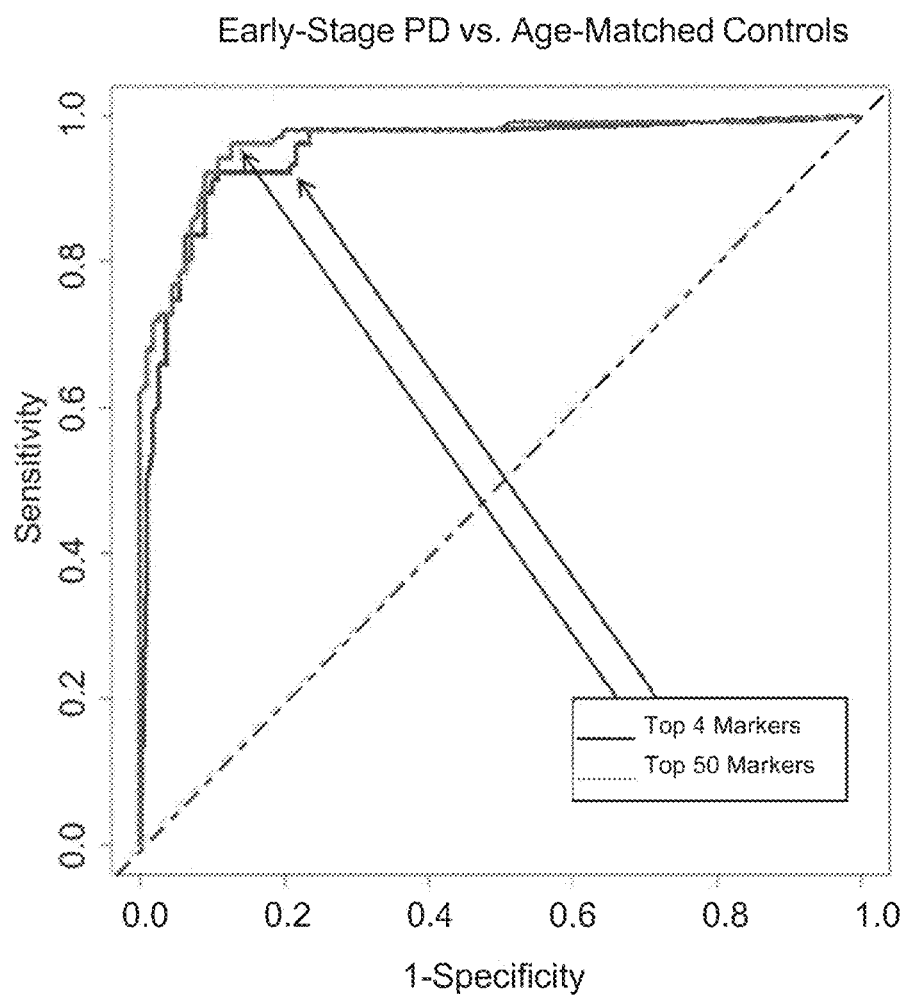
FIG. 2A and FIG. 2B are Receiver Operating Characteristic (ROC) curves showing assessment of autoantibody biomarkers for detection of Early-Stage PD. ROC curves are used to assess the utility of diagnostic tests; the further the plotted line extends into the upper left corner of the box, the better the utility of the diagnostic and the closer the Area Under the Curve (AUC) approaches a value of 1.0, which is the best result a diagnostic test can achieve.

The top 50 autoantibody biomarkers chosen from the Training Set as the Early-Stage PD diagnostic panel were then re-verified as significant predictors by *Random Forest* (*RF*) (Breiman L (2001) Random Forests. Machine Learning 45: 5-32). Upon evaluation of the Training Set samples (n=108; 52 Early-Stage PD, 56 controls) utilizing the 50 selected biomarkers, Early-Stage PD subjects were distinguished from age- and sex-matched controls with a 91.9% prediction accuracy and an Out-of-Bag (OOB) error of 8.1%. The same 50 biomarkers were then used to classify Early-Stage PD in the Testing Set, which was not involved in biomarker selection. RF was able to correctly classify Early-Stage PD in Testing Set subjects (n=106; 51 early stage PD, 55 controls) with an overall accuracy of 87.9% and an OOB error of 12.1%. Combining both Training and Testing Set samples, RF successfully distinguished Early-Stage PD from controls with an overall accuracy of 89.2% and an OOB error of 10.8% (Table 2). The diagnostic utility of the panel of 50 selected biomarkers for distinguishing Early-Stage PD subjects from age-matched controls was also interpreted using Receiver Operating Characteristic (ROC) curve analysis (Zou et al. *Circulation* 115, 654-657 (2007) (FIG. 2A). The ROC area under the curve (AUC) for this comparison was 0.93, indicating excellent classification accuracy (Table 3). The diagnostic sensitivity, specificity, and positive and negative predictive values for the 50 biomarkers are also shown (Table 2).

TABLE 2

Diagnostic results using a panel of 50 Early-Stage PD autoantibody biomarkers. The performance of the top 50 Early-Stage PD autoantibody biomarkers was assessed using RF. Combining both Training and Testing Set samples, RF successfully distinguished Early-Stage PD (N = 103) from age- and sex-matched controls, age-matched plus younger controls, mild-moderate PD, mild-moderate AD, multiple sclerosis and breast cancer with high overall accuracies. PPV, positive predictive value; NPV, negative predictive value.

Early-Stage PD (n = 103) vs.

|  | Age Matched Controls | Mild-Moderate PD | Mild-Moderate AD | Multiple Sclerosis | Breast Cancer |
|---|---|---|---|---|---|
| n | 111 | 29 | 50 | 30 | 30 |
| Sensitivity % | 94.2 | 98.1 | 98.1 | 98.1 | 98.1 |
| Specificity % | 84.7 | 100.0 | 98.0 | 93.3 | 96.7 |
| PPV % | 85.1 | 100.0 | 99.0 | 98.1 | 99.0 |
| NPV % | 94.0 | 93.6 | 96.1 | 93.3 | 93.6 |
| Overall Accuracy % | 89.2 | 98.5 | 98.0 | 97.0 | 97.7 |
| Overall Error % | 10.8 | 1.5 | 2.0 | 3.0 | 2.3 |

Figure 4:
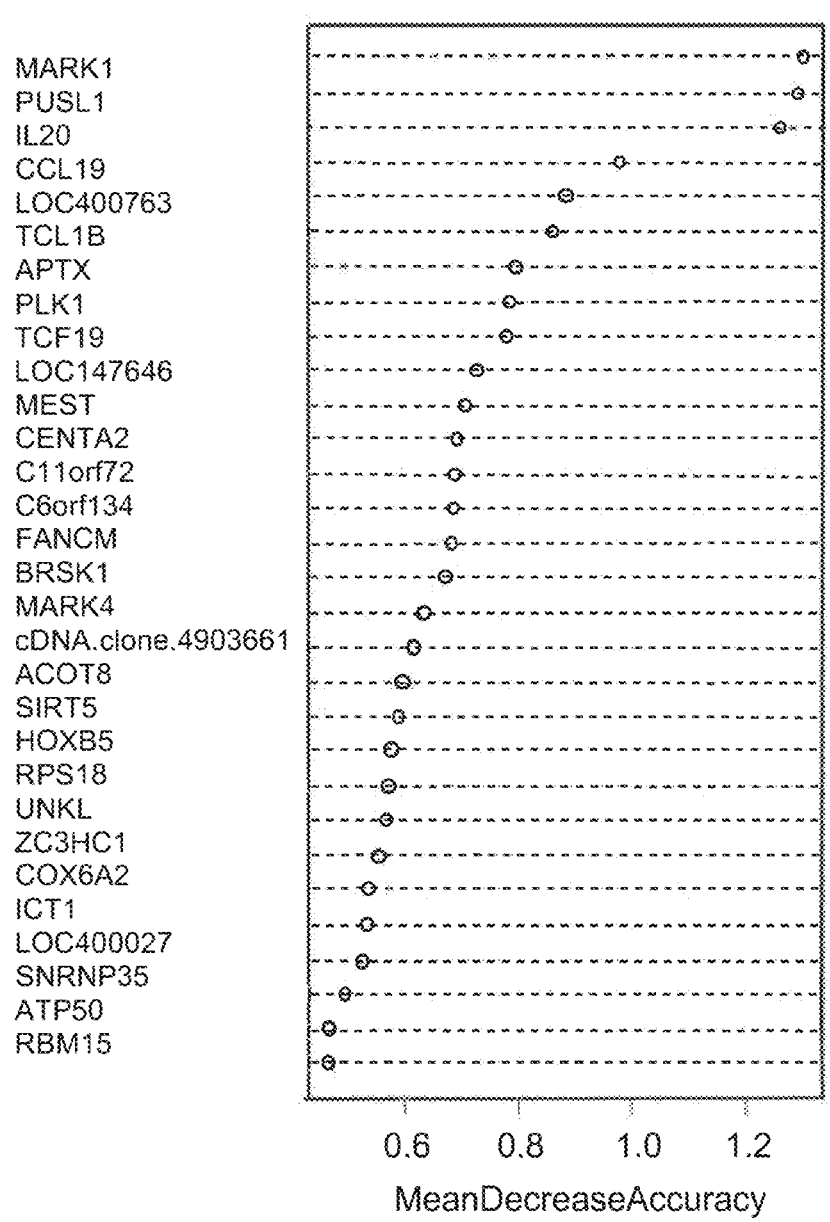
FIG. 4 is a diagram showing effect of younger controls on biomarker selection and diagnostic importance. Gini plots demonstrating the relative importance of 30 of the top 50 biomarkers to the RF classification decision when comparing age-matched controls plus younger healthy controls. Biomarkers are sorted according to decreasing relative importance from top to bottom, with the relative impact of each biomarker to the RF classification decision indicated by the extent of deflection of the indicator point to the right side of the plot. Note that the identities of the top 4 biomarkers shown in both plots are the same for both panels.

Example 4 Minimum Number of Autoantibodies Required for Accurate Early-Stage PD Diagnosis To determine the minimum number of autoantibody biomarkers required to achieve the best diagnostic accuracy, biomarkers were sorted according to decreasing relative importance from top to bottom in a Gini Plot, with more favorable diagnostic capability reflected by a greater mean decrease in accuracy (FIG. 4). Biomarkers with the lowest mean decrease in accuracy were successively removed until the overall diagnostic accuracy began to decline significantly. Using this approach, a panel of four biomarkers (top four biomarkers in Table 1) was found to be the minimum number required to maintain an effective diagnostic accuracy (ROC AUC=0.92; sensitivity=0.84; specificity=0.87) for distinguishing Early-Stage PD subjects from age-matched controls (FIG. 2A; Table 3).

Example 5 Specificity of Selected Biomarkers for Early-Stage PD

The specificity of the autoantibody biomarkers for Early-Stage PD was tested to determine if they could be used to successfully differentiate Early-Stage PD from other neurological and non-neurological diseases. To eliminate the possibility that the selected biomarkers were simply detecting non-specific CNS degeneration, the same Early-Stage PD serum samples were compared to samples from 50 patients with Alzheimer's disease (AD) and 30 samples from

TABLE 3

ROC curve analysis of diagnostic results. ROC curve analyses was used to assess the diagnostic utility of the panels of 50 and four selected biomarkers for distinguishing Early-Stage PD subjects from age-matched controls from the subject groups listed. Areas under the curve (AUC) at 95% confidence are listed along with values for sensitivity and specificity derived from the ROC curve output data.

| | 50 Markers | | | 4 Markers | | |
|---|---|---|---|---|---|---|
| Early-Stage PD (n = 103) vs. | AUC (95% CI) | Sensitivity (95% CI) | Specificity (95% CI) | AUC (95% CI) | Sensitivity (95% CI) | Specificity (95% CI) |
| Age Matched Controls (n = 111) | 0.93 (.88-.99) | 0.92 (.84-.98) | 0.87 (.78-.94) | 0.92 (.86-.97) | 0.84 (.74-.94) | 0.87 (.78-.94) |
| Age Matched and Younger Controls (n = 156) | 0.96 (.93-.98) | 0.91 (.85-.96) | 0.94 (.90-.97) | 0.96 (.93-.98) | 0.91 (.85-.96) | 0.94 (.90-.97) |
| Mild-Moderate PD (n = 29) | 0.98 (.97-1) | 0.98 (.95-1) | 1.00 | 0.99 (.97-1) | 0.98 (.95-1) | 1.00 |
| Mild-Moderate AD (n = 50) | 0.99 (.97-1) | 0.98 (.95-1) | 1.00 | 0.99 (.97-1) | 0.98 (.95-1) | 0.98 (.94-1) |
| Multiple Sclerosis (n = 30) | 0.98 (.97-1) | 0.98 (.95-1) | 1.00 | 0.99 (.97-1) | 0.98 (.95-1) | 1.00 |
| Breast Cancer (n = 30) | 0.99 (.98-1) | 0.98 (.93-1) | 1.00 | 0.99 (.97-1) | 0.98 (.95-1) | 0.97 (.90-1) |

TABLE 4

Subject demographics. For each disease group the number of individuals (n), age, range of age, gender, and ethnicity are listed. For the Early-Stage PD subjects, the Unified Parkinson's Disease Rating Scale (UPDRS) and Hoehn and Yahr scores are included as indices of PD severity.

| Group | n | Age (Years) | (Range) | Sex (% Male) | Ethnicity (% Caucasian) | UPDRS | Hoehn & Yahr |
|---|---|---|---|---|---|---|---|
| Parkinson's disease | 132 | 65.1 ± 10.3 | 37-88 | 57 | 89 | — | — |
| Early-Stage | 103 | 62.7 ± 9.3 | 37-79 | 58 | 98 | 38.1 ± 16.8 | 2.1 ± 0.6 |
| Mild-Moderate | 29 | 74.3 ± 9.0 | 53-88 | 55 | 55 | — | — |
| Controls | 156 | 55.0 ± 15.6 | 19-87 | 56 | 76 | — | — |
| Age-Matched | 111 | 63.1 ± 8.4 | 51-87 | 56 | 78 | — | — |
| Non Age-Matched | 45 | 34.9 ± 10.2 | 19-50 | 49 | 71 | — | — |
| Alzheimer's disease | 50 | 78.5 ± 8.8 | 61-97 | 42 | 88 | — | — |
| Multiple Sclerosis | 30 | 51.0 ± 9.2 | 36-67 | 33 | 97 | — | — |
| Breast Cancer | 30 | 46.9 ± 5.8 | 32-54 | 0 | 97 | — | — | patients with multiple sclerosis (MS). Using the panel of 50 biomarkers, Early-Stage PD sera were readily distinguished from AD sera with an overall accuracy of 98.0% (sensitivity=98.1%; specificity=98.0%) (Table 2). ROC curve analysis yielded an AUC of 0.99 and comparable values for sensitivity and specificity (Table 3). Using the panel of only four biomarkers yielded an overall accuracy of 97.4% (ROC AUC=0.99; sensitivity=0.98; specificity=0.98) (Table 3). Similarly, both biomarker panels were able to readily distinguish Early-Stage PD from MS subjects with comparable overall accuracy (Tables 2 and 3).

Assays were also carried out to determine the specificity of the Early-Stage PD diagnostic biomarkers in the face of non-neurological disease, in this case breast cancer. Results showed that 30 breast cancer (BC) samples were successfully differentiated from the 103 Early-Stage PD samples with an overall accuracy of 97.7% (sensitivity=98.1%; specificity=96.7%; ROC AUC=0.99) for the full panel of 50 biomarkers (Table 3). ROC analysis using the panel of four biomarkers yielded an AUC of 0.99, a sensitivity of 0.98, and a specificity of 0.97 (Table 3). These results demonstrate that the diagnostic panels of 50 and four autoantibody biomarkers were comparably accurate in differentiating Early-Stage PD from both neurological and non-neurological controls.

Example 6 Use of Selected Panels of PD Biomarkers to Stage PD Progression

In this example, assays were carried out to examine whether the selected panels of 50 and four Early-Stage PD autoantibody biomarkers could distinguish Early-Stage PD from later stages with more advanced pathology.

Figure 2B:
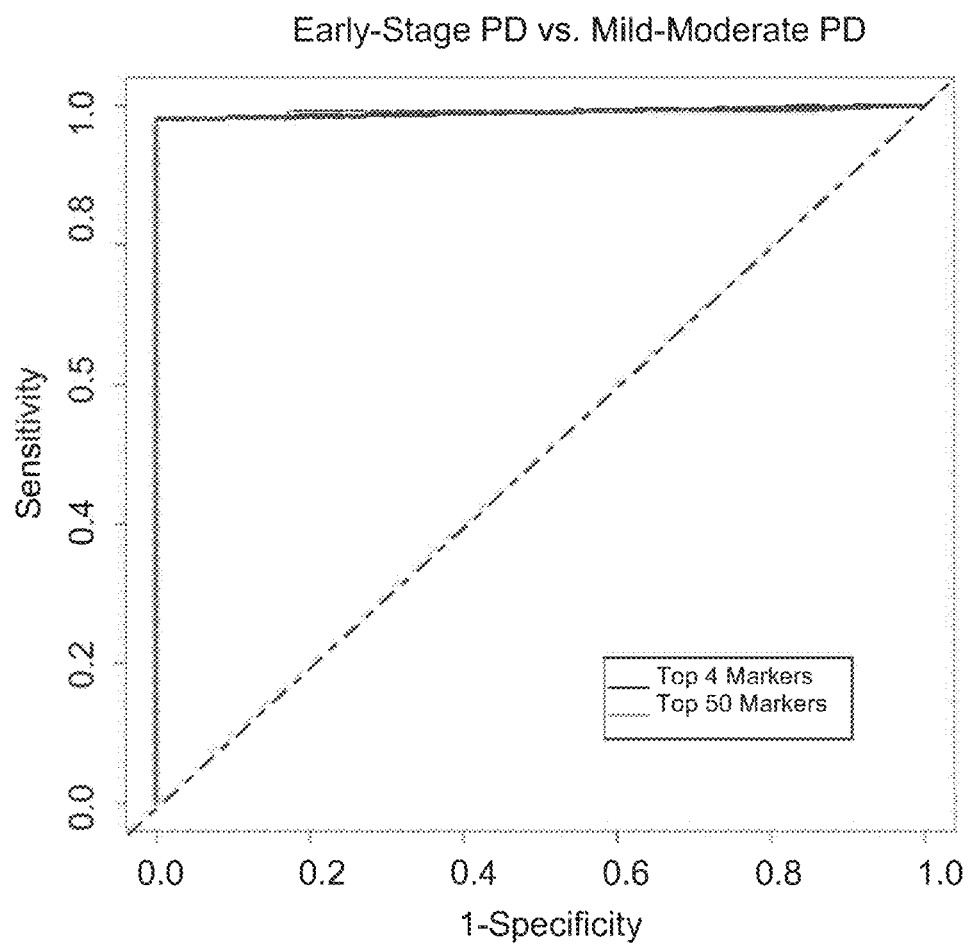

To address this, 103 Early-Stage PD serum samples were compared to 29 mild/moderate-stage PD samples using RF. Early-Stage PD samples were correctly classified with an overall accuracy of 98.5% and an OOB error of 1.5% (sensitivity=98.1%; specificity=100.0%) (Table 2) and a ROC AUC of 0.98 (FIG. 2B; Table 3) using the panel of 50 biomarkers. Comparable results were obtained with the panel of four Early-Stage PD autoantibody biomarkers (FIG. 2B; Table 3). These findings highlight the high level of specificity of these biomarker panels for the diagnosis of Early-Stage PD, and also demonstrate the potential utility of separate and specific autoantibody biomarker panels for identifying discrete stages of PD disease progression, as illustrated in FIG. 3.

Example 7 Effects of Addition of Younger Controls on Biomarker Selection and Diagnostic Accuracy There is a growing realization that most CNS diseases are preceded by long prodromal phases of ongoing, gradually escalating pathology for many years prior to the emergence of detectable symptoms (Montine et al. *Toxicologic pathology* 39, 99-102 (2011), Gaig et al. *Movement disorders: Official journal of the Movement Disorder Society* 24 Suppl 2, S656-664 (2009), Tolosa et al. *Journal of the neurological sciences* 310, 4-8 (2011), and Berendse et al. *Journal of the neurological sciences* 310, 21-24 (2011)).

This reality makes it very difficult for samples derived from the aging population to be both age-matched and unequivocally pathology-free. To investigate the impact of this potential limitation, the effects of including younger, non-age-matched controls on the initial selection of Early-Stage PD autoantibody biomarkers were tested. To accomplish this, 52 Early-Stage PD samples were compared to a control group composed of 56 age-matched and 45 additional younger, non-age-matched controls. As described above, the top 50 Early-Stage PD autoantibody biomarkers were selected in Prospector on the basis of prevalence difference between the two groups. The utility of these 50 new biomarkers for distinguishing Early-Stage PD (n=103) subjects from age-matched controls (n=111) was then verified using RF, yielding an overall diagnostic accuracy of 88.8%, a sensitivity of 93.2% and specificity of 84.7%. When all Early-Stage PD samples (n=103) were compared to all age-matched and non-age-matched controls (n=156) these biomarkers yielded an overall diagnostic accuracy of 90.4%, a sensitivity of 94.2%, and a specificity of 87.8%. These results were comparable to those obtained using the original 50 biomarkers described above. This is not surprising considering that, among the 50 new early-PD biomarkers, 32 were found to overlap with the previous set of 50 biomarkers that were derived from inclusion of only age- and sex-matched controls, and the identities of the four top biomarkers remained unchanged (FIG. 4).

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

EQUIVALENTS

One of ordinary skill in the art will recognize that there are many equivalents of the specific embodiments disclosed herein, and that those equivalents will require no more than routine experimentation in the art. Therefore, those equivalents must be considered part of this invention and as such must be considered to be covered by the following claims.

All references and citations disclosed herein are to be considered incorporated by reference in their entirety.

---

What is claimed is:

1. A method for diagnosing early-stage Parkinson's disease (PD) in a subject, the method comprising: obtaining an immunoglobulin-containing biological sample from the subject; and performing an assay to determine the amount of Early-Stage PD autoantibody biomarkers in the biological sample, wherein the assay comprises:
   (i) contacting the biological sample with a substrate attached to at least four antigens, wherein the at least four antigens comprise tRNA pseudouridine synthase-like 1 (PUSL1), serine/threonine-protein kinase MARK1, interleukin-20 (IL20), and C—C motif chemokine 19 (CCL19) antigens or antigenic fragments thereof, under conditions that allow immunocomplexes of each of the antigens or antigenic fragments thereof and a corresponding autoantibody biomarker to form, wherein the substrate comprises a plurality of beads, each bead attached to one type of antigen;
   (ii) probing the corresponding immunocomplexes with a detectable label such that the corresponding immunocomplexes are labeled; and
   (iii) detecting the amount of the labeled corresponding immunocomplexes by measuring the detecting label, wherein a higher amount of immunocomplexes of at least PUSL1, serine/threonine-protein kinase MARK1, IL20, and CCL19 or antigenic fragments thereof in the biological sample obtained from the subject relative to the amount of immunocomplexes of at least PUSL1, serine/threonine-protein kinase MARK1, IL20, and CCL19 or antigenic fragments thereof in controls identifies the subject as having Early-Stage PD.

2. The method of claim 1, wherein at least one additional antigen is selected from the group consisting of T-cell leukemia/lymphoma protein 1B (TCL1B), Serine/threonine-protein kinase PLK1 (PLK1), Transcription factor 19 (TCF19), Uncharacterized protein C11orf52 (C11orf72), Arf-GAP with dual PH domain-containing protein 2 (ADAP2), Alpha-tubulin N-acetyltransferase 1 (ATAT1), NAD-dependent protein deacylase sirtuin-5, mitochondrial (SIRT5), Serine/threonine protein kinase BRSK1, MOB kinase activator 3C (MOB3C), RNA pseudouridylate synthase domain-containing protein 2 (RPUSD2), Fanconi anemia group M protein (FANCM), Lysine-specific demethylase 4D (KDM4D), Cytochrome c oxidase subunit A2 (COX6A2), Acyl-coenzyme A thioesterase 8 (ACOT8), U11/U12 small nuclear ribonucleoprotein 35 kDa protein (SNRNP35), ATP synthase subunit O (ATP5O), Peptidyl-tRNA hydrolase (ICT1), Homo sapiens zinc finger, C3HC-type containing 1 (ZC3HC1), Wilms tumor upstream neighbor 1 (WT1-AS), hypothetical protein LOC150577 (LOC150577), Translational activator of cytochrome c oxidase 1 (TACO1), Zinc finger protein 808 (ZNF808), Bifunctional 3'-phosphoadenosine 5'-phosphosulfate synthase 2 (PAPSS2), 60S ribosome subunit biogenesis protein (NIP7), Regulator of G-protein signaling 13 (RGS13), Homo sapiens hypothetical protein LOC147646 (LOC147646), Homo sapiens hypothetical LOC388528 (LOC388528), Homo sapiens hypothetical LOC150371 (LOC150371), Putative chondrosarcoma-associated gene 1 protein (CSAG1), cDNA clone BC103660, AP/microtubule affinity-regulating kinase 4, Mesoderm-specific transcript homolog protein (MEST), Human cDNA ORF Clone (C11orf72), *Macaca fascicularis* brain cDNA clone (QorA-12280), *Macaca fascicularis* brain cDNA clone (QorA-10370), 40S ribosomal protein S18 (RPS18), Putative E3 ubiquitin-protein ligase UNKL (UNKL), Protein BUD31 homolog (BUD31), *Homo sapiens* hypothetical LOC400763 (LOC400763), HCG1986256, *Homo sapiens* hypothetical LOC400027 (LOC400027), *Homo sapiens* homeobox B5 (HOXB5), Tubulin polyglutamylase TTLL1, 39S ribosomal protein L19, mitochondrial (MRPL19), MAP kinase-activated protein kinase 5 (MAPKAPK5), and Exosome complex component RRP40 (EXOSC3), or any antigenic fragment thereof.

3. The method of claim 1, wherein the plurality of beads are magnetic or non-magnetic beads.

4. The method of claim 3, wherein the magnetic or non-magnetic beads are polymer or glass beads.

5. The method of claim 1, wherein the biological sample is serum, plasma, whole blood, CSF, saliva, or sputum.

6. The method of claim 1, wherein the assay distinguishes early-stage PD subjects from advanced PD, mild-moderate PD, non-PD, and control subjects by detecting the amounts of the labeled corresponding immunocomplexes from the biological sample and in controls.

7. The method of claim 6, wherein the non-PD condition is selected from the group consisting of Alzheimer's disease, multiple sclerosis, and cancer.

8. A kit comprising: four or more antigens that are specific for Early-Stage PD autoantibody biomarkers, the four or more antigens attached to a substrate comprising a plurality of beads, each bead linked to one type of antigen; and reagents for detecting binding of the antigens to the Early-Stage PD autoantibody biomarkers present in a biological sample, wherein the antigens comprise tRNA pseudouridine synthase-like 1 (PUSL1), serine/threonine-protein kinase MARK1, interleukin-20 (IL20), and C—C motif chemokine 19 (CCL19) or antigenic fragments thereof.

9. The kit of claim 8, wherein the plurality of beads are polymer or glass beads.

* * * * *